(12) United States Patent
Cheng et al.

(10) Patent No.: US 8,771,402 B2
(45) Date of Patent: Jul. 8, 2014

(54) MEMBRANE BASED APPARATUS FOR MEASUREMENT OF VOLATILE PARTICLES

(75) Inventors: Meng-Dawn Cheng, Oak Ridge, TN (US); Steve L. Allman, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 206 days.

(21) Appl. No.: 13/523,067

(22) Filed: Jun. 14, 2012

(65) Prior Publication Data

US 2013/0186269 A1 Jul. 25, 2013

Related U.S. Application Data

(60) Provisional application No. 61/496,632, filed on Jun. 14, 2011.

(51) Int. Cl.
*B01D 53/22* (2006.01)
(52) U.S. Cl.
USPC .......... 95/47; 95/43; 95/45; 95/50; 96/4
(58) Field of Classification Search
USPC ............................. 95/43, 45, 47, 50; 96/4
See application file for complete search history.

(56) References Cited

U.S. PATENT DOCUMENTS

| | | | | |
|---|---|---|---|---|
| 5,854,077 A * | 12/1998 | Wolfson et al. | ............... | 436/110 |
| 5,983,732 A * | 11/1999 | Hering et al. | ............... | 73/863.22 |
| 6,062,210 A * | 5/2000 | Welles | ............... | 126/208 |
| 6,289,888 B1 * | 9/2001 | Welles | ............... | 126/263.01 |
| 6,503,758 B1 * | 1/2003 | Allen et al. | ............... | 436/110 |
| 6,764,857 B2 * | 7/2004 | Allen et al. | ............... | 436/110 |
| 6,852,543 B2 * | 2/2005 | Allen et al. | ............... | 436/122 |
| 7,135,295 B1 * | 11/2006 | Willner et al. | ............... | 435/7.1 |
| 7,427,311 B2 * | 9/2008 | Burtscher et al. | ............... | 95/23 |
| 7,682,426 B2 * | 3/2010 | Burtscher et al. | ............... | 95/288 |
| 7,867,779 B2 * | 1/2011 | McDermott et al. | ............... | 436/181 |
| 7,964,411 B2 * | 6/2011 | Dasgupta et al. | ............... | 436/161 |
| 8,333,811 B2 * | 12/2012 | Hatziemmanouil | ............... | 44/307 |
| 8,603,796 B2 * | 12/2013 | Look et al. | ............... | 435/235.1 |
| 2003/0040120 A1 * | 2/2003 | Allen et al. | ............... | 436/110 |
| 2003/0138965 A1 * | 7/2003 | Allen et al. | ............... | 436/110 |
| 2004/0202578 A1 * | 10/2004 | Burtscher et al. | ............... | 422/83 |

(Continued)

OTHER PUBLICATIONS

Cheng, M.D., et al., "Improved measurement for volatile particles: Vapor-particle separator design and laboratory tests", American Institute of Physics, Review of Scientific Instruments, Dec. 2011, vol. 82, pp. 1-8.

(Continued)

*Primary Examiner* — Jason M Greene
*Assistant Examiner* — Anthony Shumate
(74) *Attorney, Agent, or Firm* — Scully, Scott, Murphy & Presser, P.C.

(57) ABSTRACT

A vapor particle separator including a temperature controlled chamber for desorbing vapors from the particulates of an exhaust gas and a separation chamber including a micro porous membrane. The micro porous membrane provides an interface between at least one particle passageway and at least one vapor passageway through the separation chamber. The particle passageway extends from an entrance to the separation chamber to a particle exit from the separation chamber. The vapor passageway extends from the micro-porous membrane to a vapor exit from the separation chamber that is separate from the particle exit from the separation chamber.

28 Claims, 8 Drawing Sheets

(56) References Cited

U.S. PATENT DOCUMENTS

| | | | |
|---|---|---|---|
| 2005/0059157 A1* | 3/2005 | Allen et al. | 436/110 |
| 2006/0172428 A1* | 8/2006 | McDermott et al. | 436/63 |
| 2007/0006728 A1* | 1/2007 | Burtscher et al. | 95/23 |
| 2008/0206281 A1* | 8/2008 | Look et al. | 424/211.1 |
| 2009/0313887 A1* | 12/2009 | Hatziemmanouil | 44/307 |
| 2013/0192463 A1* | 8/2013 | Wu et al. | 95/82 |
| 2013/0239808 A1* | 9/2013 | Wu et al. | 95/129 |

OTHER PUBLICATIONS

Phelps, T.J., et al., "Micron-pore-sized metallic filter tube membranes for filtration of particulates and water purification", Journal of Microbiological Methods, Jul. 2008, vol. 74, pp. 10-16.

* cited by examiner

NUMBER SHOWS THE DISTANCE FROM THE SAMPLE INLET IN INCH

MEMBRANE BASED APPARATUS FOR MEASUREMENT OF VOLATILE PARTICLES

STATEMENT REGARDING FEDERALLY SPONSORED RESEARCH OR DEVELOPMENT

This invention was made with government support under Contract Number DE-AC05-00OR22725 between the United States Department of Energy and UT-Battelle, LLC. The U.S. government has certain rights in this invention.

CROSS-REFERENCE TO RELATED APPLICATIONS

This application claims priority from U.S. Provisional Application No. 61/496,632, filed Jun. 14, 2011, which is herein incorporated by reference in its entirety.

FIELD OF THE INVENTION

The present disclosure relates to methods for separating particles and vapors from exhaust gasses and apparatuses directed thereto.

BACKGROUND

A thermodenuder is a device that enables the study of the volatility of engine combustion particles that are found in the exhaust of the engine. For example, aircraft engine exhaust is a complex mixture of gaseous molecules and ultrafine particulate matter. Depending on the combustion conditions and the fuel burned, large fractions of the materials present in the exhaust could be semi-volatile in nature. It is believed that condensation of semi-volatile species onto the particles is responsible for the formation of volatile particles in the exhaust plume downstream from the engine exhaust nozzle. Heavier polyaromatic hydrocarbons, for example, is one class of species that participates in the condensation. Fuel sulfur is another fuel constituent of volatile species in engine exhaust.

SUMMARY OF THE INVENTION

In one embodiment of the present disclosure, a vapor particle separator is provided that includes a temperature controlled chamber for desorbing vapors (also referred to as gas phase molecules) from the particulates of an exhaust gas, and a separation chamber including a micro porous membrane for separating the particulates from the vapors that are desorbed from the particulates in the temperature controlled chamber. The micro porous membrane provides an interface between a particle passageway and a vapor passageway through the vapor particle separator. The micro porous membrane has a pore size that allows for diffusion through the micro porous membrane of the vapors having a higher diffusivity than the particulates. The particle passageway extends from an entrance to the separation chamber to a particle exit from the separation chamber. The vapor passageway extends from the entrance to separation chamber to a vapor exit from the separation chamber, wherein the vapor exit from the separation chamber is separate from the particle exit from the separation chamber.

In another aspect of the present disclosure, a method of separating vapors from particles is provided that utilizes a vapor particle separator including a micro porous membrane. In one embodiment, the method may include collecting particulates of an exhaust gas from an exhaust plume of an engine, and heating the particles of the exhaust gas in a temperature controlled chamber of a vapor particle separator. The temperature of the temperature controlled chamber may be selected to desorb gas phase molecules from the particulates of the exhaust gas. The particulates of the exhaust gas and the gas phase molecules that were desorbed from the particulates of the exhaust gas may then be introduced to a separation chamber of the vapor particle separator. The separation chamber may include a particle passageway to a particle exit in a first direction and a vapor passageway to a vapor exit in a second direction, wherein an interface between the particle passageway and the vapor passageway is provided by a micro porous membrane. A cross flow may be applied to the separation chamber to draw the vapors from the vapor exit of the vapor particle separator and to draw the particles of the exhaust gas from the particle exit of the vapor particle separator.

BRIEF DESCRIPTION OF THE DRAWINGS

The following detailed description, given by way of example and not intended to limit the disclosure solely thereto, will best be appreciated in conjunction with the accompanying drawings, wherein like reference numerals denote like elements and parts, in which.

DETAILED DESCRIPTION

Figure 1:
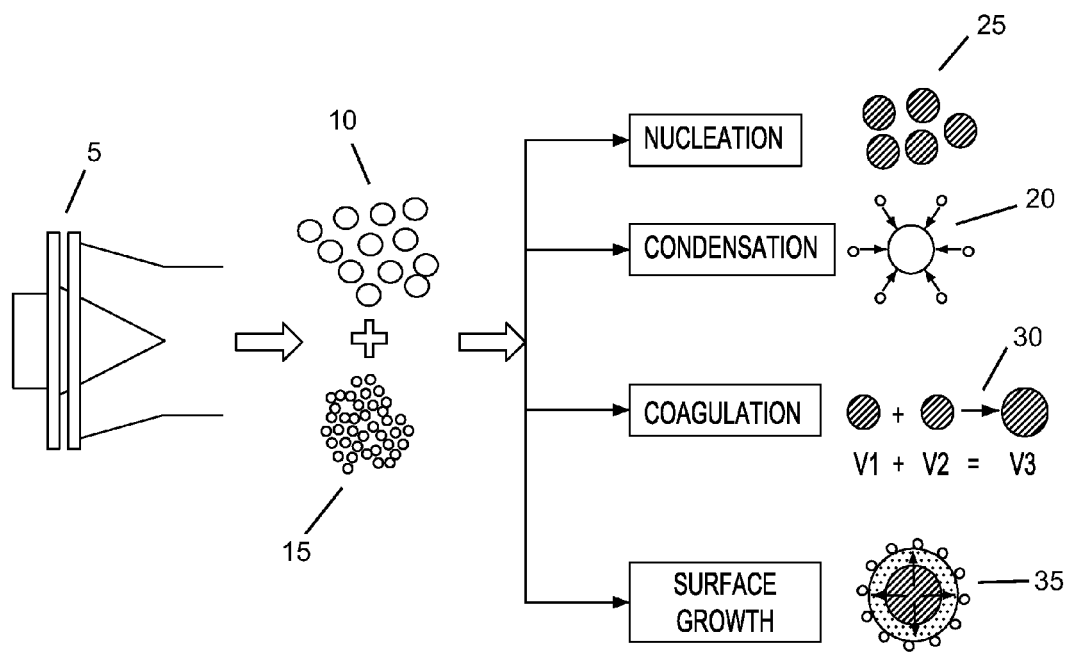
FIG. 1 is a flow chart depicting some embodiments of the mechanisms of formation of volatile particulates from the exhaust flow of an engine, in accordance with the present disclosure.

Detailed embodiments of the present disclosure are described herein; however, it is to be understood that the disclosed embodiments are merely illustrative of the compositions, structures and methods of the disclosure that may be embodied in various forms. In addition, each of the examples given in connection with the various embodiments are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the compositions, structures and methods disclosed herein. References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment.

Combustion particulates (also referred to as combustion particles) from engines, such as gasoline engines, diesel engines and jet engines, can be broadly classified as condensable and non-volatile fractions. The combustion particles (also referred to as engine particles or engine combustion particles) can be ultrafine, i.e., having a nanoscale diameter. Ultrafine engine combustion particles can be more toxic than larger engine combustion particles due to their large surface area per unit mass and small size. The surface area and size of the ultrafine engine combustion particles may enable such ultrafine particles to translocate once they have been inhaled. Typically, when engine combustion particles are heated to sufficiently high temperature, the condensable fraction of the engine combustion particle will vaporize, which can lead to complex aerosol dynamics involving instantaneous formation, removal and surface reactions. For example, when heated, the condensable fraction of the engine combustion particles may be vaporized at a given temperature at which the non-volatile fraction can remain "in the condensed phase" as a solid or in a non-vapor phase.

Further, nanoparticles, i.e., particles having a diameter that is smaller than 50 nm, have different material properties from their larger counterpart. In some instances, the fundamental change of atom confinement and packing in nanoparticles leads to a change in the material properties that is also a possible cause of nanotoxicity. For example, the temperature at which nanoparticles vaporize may be different from that of the same material at a larger size. Exposure of the engine combustion particles to changing temperatures can create a change in the particles size from a nano-sized regime to a macro size regime.

For example, once the engine exhaust mixes with the colder ambient air, high molecular weight vapor molecules, i.e., gas phase molecules, in the exhaust plume condense onto the non-volatile fraction (or soot), changing the particle size distribution. Given sufficient concentration the vapors, i.e., gas phase molecules, can form new particles through condensation nucleation processes that could change the particle size distribution of the engine combustion particles.

FIG. 1 depicts some examples of mechanisms that cause variations in the particle size distribution of engine combustion particles 10 emitted in the exhaust gasses of a jet engine. In some embodiments, engine combustion particles 10 emitted by an engine 5, such as a jet engine, in an exhaust plume are mixed in ambient air with gas phase molecules 15, i.e., gas phase molecules, which are also emitted by the engine 5. For example, the exhaust from the engine 5 may include a large number of chemical species in both gas phases, i.e., gas phase species 15, and particulate phases, i.e., engine combustion particles 10, in which some are condensibles at ambient temperature. The gas phase is a highly complex mixture that consist of unburned fuel species, combustion by-products as well as combustion-derived higher molecular-weight organic species. In this mixture, a diverse range of volatility exists. By operational definition, some are considered as volatile and some are semi-volatile. As used herein, the term "semi-volatile species" include both gas phases, i.e., gas phase species 15, and particulate phases, i.e., engine combustion particles 10, that have a vapor pressure from $10^{-4}$ atm to $10^{-11}$ atm at room temperature (20° C.). As used herein, the term "volatile species" denotes both gas phases, i.e., gas phase species 15, and particulate phases, i.e., engine combustion particles 10, having a vapor pressure that is greater than $10^{-4}$ atm at room temperature (20° C.).

In engine exhaust, combustion byproducts, e.g., the gas phase species 15 and engine combustion particles 10, encounter relatively cold temperature, e.g., temperature of the ambient air, in a very short period. For example, the temperature change of the combustion byproducts as they reach the ambient air may range from 400° C./min to 800° C./min in micro seconds. The partition of volatile and semi-volatile species in engine exhausts reaching the ambient air is rapid. In some examples, condensible species transfer mass onto existing nucleic through heterogeneous condensation 20 or form new particles through nucleated condensation 25, as depicted in FIG. 1. Other phenomena that may effect the particle size distribution include coagulation 30 and surface growth 35. Coagulation is the formation of a larger chemical species that results from collisions of two smaller chemical species. Surface growth is a process by which gas-phase molecules react with soot particles or deposit on the surface of the particles thereby effectively transfer the mass from the gas phase to the particulate phase.

Prior thermodenuder devices either do not remove the vapor phase species, i.e., gas phase molecules, or apply some kind of adsorbent to captures the vapor phase species such that they would not condense onto the engine combustion particles. The vapor phase species could include the molecules that are thermally desorbed from engine combustion particles in the thermodenuder or those that are present in the vapor phase when entering the thermodenuder. One of the problems that have been discovered with the adsorbent based thermodenuders is that in engine exhaust, the quantity of the volatile species is high and it could deplete the adsorbent capacity of the thermodenuder without warning. Further, artifacts can be produced in adsorbent based thermodenuder devices and an erroneous particle size distribution can be generated due to the inability of such a technique to separate vapors, i.e., gas phase molecules, from non-volatile soot particles. It has been determined that the above described thermodenuders experience a size dependent loss of particles ranging from 15% to 85%. Since the loss is particle size dependent, it is difficult to correct for loss, making an accurate qualification of source emissions impossible with thermodenuders experiencing this level of particle loss.

In view of the observed disadvantages of thermodenuders that employ adsorbents and thermodenuders that fail to separate the vapor phase species, i.e., gas phase molecules, from the engine combustion particulates, it can be advantageous for a thermodenuder to provide substantially zero particle loss, controlled phase separation at a controllable temperature, and sample collection for analytical measurement of both gas and particulate phases. In contrast to thermodenuder designs that apply solid adsorbent as the means of removing desorbed vapor, i.e., gas phase molecules, from the engine combustion particles, the methods and structures disclosed herein apply the principle of membrane separation in a counter flow filtration design to remove vapors and prevent re-condensation of desorbed vapor, i.e., gas phase molecules. This approach not only effectively separates the desorbed vapors from the engine combustion particles, but also enables collection of vapor, e.g., by canisters, solid phase extraction cartridges, etc., separate from the collection of the engine combustion particles. The collected vapor, i.e., gas phase molecules, may be analyzed chemically. Operationally, in some embodiments, the methods and structures provided by the present disclosure removes the vapors, i.e., gas phase molecules, before they have a chance to condense of the engine combustion particles from which they were desorbed. For example, the methods and structures disclosed herein may employ a sweeping gas, such as dry nitrogen or argon, to remove the gas phase molecules, i.e., vapors, from the separator chamber of the vapor particle separator into a detector for subsequent chemical analysis. Further, in some embodiments, the methods and structures disclosed herein replace the function of the solid adsorbents with a micro-porous membrane, therefore eliminating the need to replace adsorbents when their adsorption properties have been expended.

Figure 2:
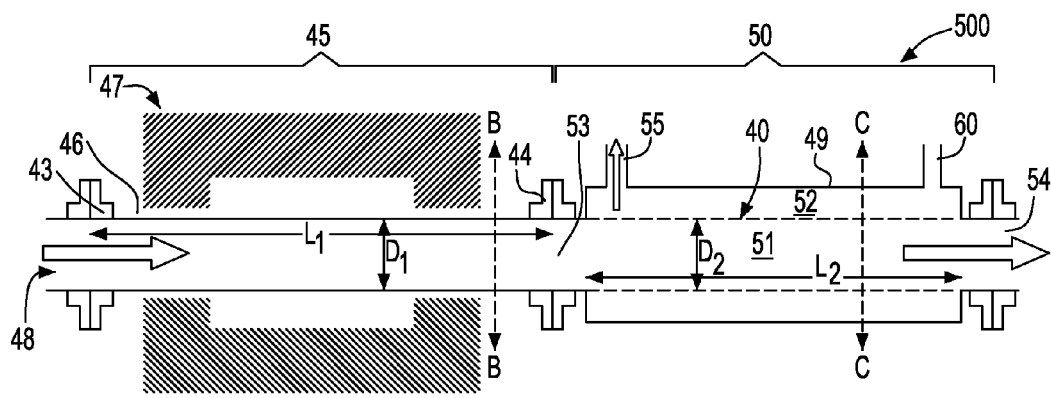
FIG. 2 is a side cross-sectional schematic view of a vapor particle separator, in accordance with one embodiment of the present disclosure.

FIG. 2 depicts one embodiment of the vapor particle separator 500 that employs a micro porous membrane 40 to separate vapors, i.e., gas phase molecules, from the particulates of an exhaust gas (also described as engine combustion particles), such as the exhaust gas of a jet engine. Although the following description refers to the exhaust gas of a jet engine, the present disclosure is not limited to only this application. For example, the exhaust gas of diesel, gas engines, turbines or any other combustion engine that produces engine combustion particles may be used in combination with the vapor particle separator 500 disclosed herein.

In one embodiment, the vapor particle separator 500 includes a temperature controlled chamber 45 for desorbing vapors, i.e., gas phase molecules, from the particulates of an exhaust gas, i.e., engine combustion particles, that enter the vapor particle separator 500. In some embodiments, the temperature controlled chamber 45 allows for vapors, i.e., gas phase molecules, to be thermally desorbed from the semi-volatile and volatile condensed particulate phases that are formed via the nucleation, condensation, coagulation, and surface growth mechanisms experienced by the engine combustion particles as they are expelled from the engine as exhaust gasses and cooled by the ambient air, as described above with reference to FIG. 1.

In one embodiment, the temperature controlled chamber 45 includes a metallic tube 46 that is positioned within a heater 47. The metallic tube 46 is typically composed of a metal, such as stainless steel, aluminum, copper, titanium, zirconium or combinations thereof. In some embodiments, the composition of the metallic tube 46 is selected to be chemically inert. In some embodiments to provide a chemically inert metallic tube 46, the metal composition of the metallic tube 46 is selected to be stainless steel. The stainless steel composition may be selected from the group consisting of UNS# S30400 (SST-304), UNS# S30403 (SST-304L), UNS# S31600 (SST-316), UNS# S31603 (SST-316L), UNS# S32100 (SST-321), UNS# S32100 (SST-321), UNS# N08330 (SST-330), UNS# S34700 (SST-347), UNS# S41000 (SST-410), UNS# S43000 (SST-430) and combinations thereof.

The metallic tube 46 provides the sample inlet 48 to the temperature controlled chamber 45 of the vapor particle separator 500 and continuously extends to the entrance of the separation chamber 50 of the vapor particle separator 50. The dimensions for the metallic tube 46 may vary depending upon the application of the vapor particle separator 500. In one embodiment, the metallic tube 46 that is present in the temperature controlled chamber 45 may have a length L1 ranging from 20 cm to 50 cm. In another embodiment, the metallic tube 46 that is present in the temperature controlled chamber 45 may have a length L1 ranging from 25 cm to 40 cm. In yet another embodiment, the metallic tube 46 may have a length L1 ranging from 30 cm to 35 cm.

The metallic tube 46 may have a cross-section across the length L1 of the metallic tube 46 with a substantially circular diameter, or the metallic tube 46 may have a multi-sided cross-section across the length L1 of the metallic tube 46. By "across the length" it is meant that the cross-section is along section line B-B, as depicted in FIG. 2. By substantially circular it is meant that the geometry of the cross section can be circular or oblong. Examples of multi-sided geometries for the cross-sections of the metallic tube 46 include square, rectangular, pentagon and octagon shaped geometries. It is noted that the aforementioned geometries for the cross section of the metallic tube 46 across its length L1 are provided for illustrative purposes only, and are not intended to limit the present disclosure, and any geometry that provides a passageway through the heat controlled chamber 45 to the separation chamber 50 is suitable for use with the present disclosure. In one embodiment, in which the metallic tube 46 has circular cross-section geometry, the inner diameter D1 of the metallic tube 46 may range from 1.5 cm to 5.0 cm. In another embodiment, the inner diameter D1 of the metallic tube 46 may range from 2.0 cm to 4.0 cm. In yet another embodiment, the inner diameter D1 of the metallic tube 46 may range from 2.5 cm to 3.5 cm.

The metallic tube 46 may include a first flange 43 for attachment to a probe for collecting exhaust gasses from an engine, and a second flange 44 for connecting the metallic tube 46 of the temperature controlled chamber 45 to the separation chamber 50. In one embodiment, the first and second flanges 43, 44 provide for engagement to the probe and the separation chamber 50 through mechanical fasteners, such as nuts, bolts and gaskets. In some embodiments, the first and second flange 43, 44 may provided for threaded engagement of the metallic tube 46 to the probe and the separation chamber 50.

The heat controlled chamber 45 typically includes a heater 47 that surrounds the metallic tube 46. In some embodiments, the heater 47 is a radiant heater. A radiant heater can discharge long-wave infrared radiation, which strikes a solid object nearby, such as the metallic tube 46, and heats it. In some embodiments, the radiant heater that provides the heater of the heat controlled chamber 45 is a ceramic radiant heater. In some embodiments, the ceramic component of the ceramic radiant heater may include at least one of ceramic metallic alloys (cermet), silicon carbide (SiC), and silica ($SiO_2$). The power of the heating elements may range from 400 watts to 750 watts. In another embodiment, the power of the heating elements may range from 450 watts to 700 watts. In on example, the heater 47 is a 600 watt ceramic radiant heater.

In some embodiments, the ceramic radiant heater includes a refractory lined furnace that surrounds the metallic tube 46 to provide a heating chamber. Examples of refractory materials that are suitable for providing the heating chamber include silica ($SiO_2$), zirconia ($ZrO_2$), alumina ($Al_2O_3$), chromia ($Cr_2O_3$), magnesia (MgO), dolomite and carbon. It is noted that the present disclosure is not limited to radiant heating as the means to control the temperature of the heat controlled chamber 45. For example, other forms of heaters and furnaces have been contemplated for use with the present disclosure, such as the microwave or infrared heating.

In some embodiments, the heating element of the heater 47 is selected so that the temperature of the interior of the metallic tube 46 can be increased to a temperature that desorbs vapors from the particulates of an exhaust gas, i.e., engine combustion particles, that enters the vapor particle separator 500. As used herein, the terms "desorb", "desorbs", "desorption" and derivatives thereof mean to remove an absorbed or adsorbed substance. In some embodiments, desorption of the vapors, i.e., gas phase molecules, from the engine combustion particles is provided by increasing the heat of the particles, i.e., semi-volatile or volatile particles, until the condensed portion of the particles changes from a solid phase to a gas phase.

More specifically, in some embodiments, the particulates of the exhaust gas that enter the vapor particle separator 500 include volatile and semi-volatile chemical species that are formed by at least one mechanism, such as nucleation, condensation, coagulation and surface growth, as engine combustion particulates mix with gas phase species in a rapidly cooling atmosphere from the higher temperature environment of engine to the lower temperature environment of the ambient air. As discussed above, in some embodiments, as the mixture of the engine combustion particulates mix with the gas phase species in a cooling ambient that results from the exhaust plume contacting the ambient air, the gas phase species may condense onto the engine combustion particles changing the particle size distribution of the engine combustion particles. In some embodiments, the temperature of the temperature control chamber 45 is selected to increase the temperature of the particles contained within the metallic tube 46 to the temperature that the particles were at in the exhaust leaving the engine before having their temperature reduced by the ambient air. By increasing the temperature of the particles, i.e., engine combustion particles, the solid condensation of the gas phase molecules, which provides a semi-volatile or volatile component of the engine combustion particles, is returned to its gas phase, and is hence desorbed from the engine combustions particles. Desorbing the condensed gas phase molecules, i.e., semi-volatile or volatile species, can reduce the engine combustion particles to their original particle size distribution.

In some embodiments, the heater 47 increases the temperature of the interior of the metallic tube 46 that is present in the controlled heating chamber 45 to a temperature that ranges from 200° C. to 450° C. In another embodiment, the heater 47 increases the temperature of the interior of the metallic tube 46 that is present in the controlled heating chamber 45 to a temperature that ranges from 250° C. to 400° C. In yet another embodiment, the heater 47 increases the temperature of the interior of the metallic tube 46 that is present in the controlled heating chamber 45 to a temperature that ranges from 300° C. to 500° C. It is noted that the present disclosure is not limited to the above noted temperatures, as other temperatures may be employed depending upon the application for the vapor particles separator 500.

Figure 3:
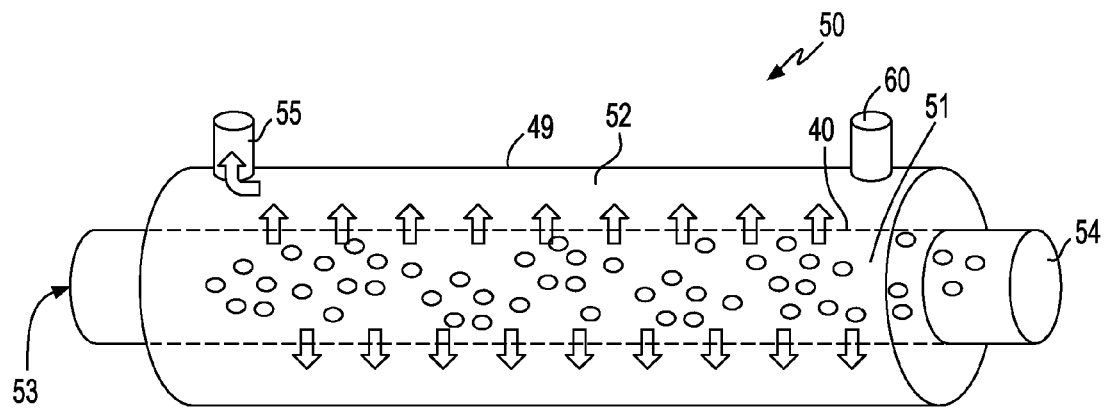
FIG. 3 is a perspective pictorial view depicting one embodiment of the separation chamber of the vapor particle separator depicted in FIG. 2.

Referring to FIGS. 2 and 3, in some embodiments, the micro-porous membrane 40 of the separation chamber 50 provides the mechanism for separating the gas phase molecules (vapors) that were desorbed from the engine combustion particles in the temperature controlled chamber 45 of the vapor particle separator 500. The micro-porous membrane 40 enables separate extraction of the engine combustion particles and the vapors desorbed of the molecules of the vapor desorbed from the engine combustion particles. The gas phase molecules have a higher diffusivity than the engine combustion particles. The higher diffusivity of the gas phase molecules allows the gas phase molecules to diffuse through the micro-porous membrane 40, wherein the micro-porous membrane 40 acting as a surface barrier prevents the engine combustion particles having a lower diffusivity from diffusing through the micro porous membrane.

In one embodiment, the micro-porous membrane 40 provides an interface between at least one particle passageway 51 through the separation chamber 50 and at least one vapor passageway 52 through the separation chamber 50. The particle passageway 51 extends from an entrance 53 to the separation chamber 50 to a particle exit 54 from the separation chamber 50. The vapor passageway 52 extends from the micro-porous membrane 40 to a vapor exit 55 from the separation chamber 50 that is separate from the particle exit 54 of the separation chamber 50.

In one embodiment, the micro porous membrane 40 has a tube geometry, wherein one of the at least one particle passageway 51 is centrally positioned in the separation chamber 50. The micro-porous membrane 40 continuously extends from the particle entrance 53, which provides the entrance to the separation chamber 50, to the particle exit 54, which is present at the exit of the separation chamber 50. The dimensions for the length L2 and width, e.g., diameter D2, of the micro porous membrane 40 may vary depending upon the application of the vapor particle separator 500. In one embodiment, the micro porous membrane 40 may have a length L2 ranging from 20 cm to 50 cm. In another embodiment, the micro porous membrane 40 that is present in the separation chamber 50 may have a length L2 ranging from 25 cm to 40 cm. In yet another embodiment, the separation chamber 50 may have a length L2 ranging from 30 cm to 35 cm.

The micro porous membrane 40 may have a cross-section across the length L2 of the micro porous membrane 40 with a substantially circular diameter, as depicted in FIG. 3, or the micro porous membrane 40 may have a multi-sided cross-section across the length L2 of the micro porous membrane 40. By "across the length" it is meant that the cross-section is along section line C-C, as depicted in FIG. 2. By substantially circular it is meant that the geometry of the cross section can be circular or oblong. Examples of multi-sided geometries for the cross-sections of the micro porous membrane 40 include square, rectangular, pentagon and octagon shaped geometries. It is noted that the aforementioned geometries for the cross section of the micro porous membrane 40 across its length L2 are provided for illustrative purposes only, and are not intended to limit the present disclosure, and any geometry that provides a passageway through the separation chamber 50 is suitable for use with the present disclosure.

In one embodiment, in which the micro porous membrane 40 has circular cross-section geometry, the inner diameter D2 of the micro porous membrane 40 may range from 1.5 cm to 5.0 cm. In another embodiment, the inner diameter D2 of the micro porous membrane 40 may range from 2.0 cm to 4.0 cm. In yet another embodiment, the inner diameter D2 of the micro porous membrane 40 may range from 2.5 cm to 3.5 cm.

The micro porous membrane 40 has a pore size that allows for diffusion of the gas phase molecules, i.e., vapors, that are desorbed from the engine combustion particles from the particle passageway 51 through the micro porous membrane 40 to the vapor passageway 52. The engine combustion particles having a lower diffusivity than the gas phase molecules, i.e., vapors, are obstructed from entering the vapor passageway 52. The term "micro-porous" as used to describe the micro porous membrane 40 means that the pore size of the microporous membrane ranges from 1 nm to 100,000 nm. In one embodiment, the micro porous membrane 40 has a pore size ranging from 5 nm to 50,000 nm. In another embodiment, the micro porous membrane 40 has a pore size ranging from 1 nm to 7 nm. In some embodiments, the micro porous membrane 40 has a wall thickness ranging from 0.25 mm to 1 mm. In another embodiment, the micro porous membrane 40 has a wall thickness ranging from 0.5 mm to 0.75 mm.

In some embodiments, the structural integrity of the micro porous membrane 40 can resist pressures greater than 300 kPa. In another embodiment, the structural integrity of the micro porous membrane 40 can resist pressures greater than 400 kPa. In yet another embodiment, the structural integrity of the micro porous membrane 40 can resist pressures greater than 450 kPa.

The micro porous membrane 40 may be composed of a metal, such as stainless steel, aluminum, titanium, zirconium and a combination thereof. In the embodiments, in which the micro porous membrane 40 is stainless steel, the composition of the stainless steel may be selected from the group consisting of UNS# S30400 (SST-304), UNS# S30403 (SST-304L), UNS# S31600 (SST-316), UNS# S31603 (SST-316L), UNS# S32100 (SST-321), UNS# S32100 (SST-321), UNS# N08330 (SST-330), UNS# S34700 (SST-347), UNS# S41000 (SST-410), UNS# S43000 (SST-430) and combinations thereof.

Figure 4:
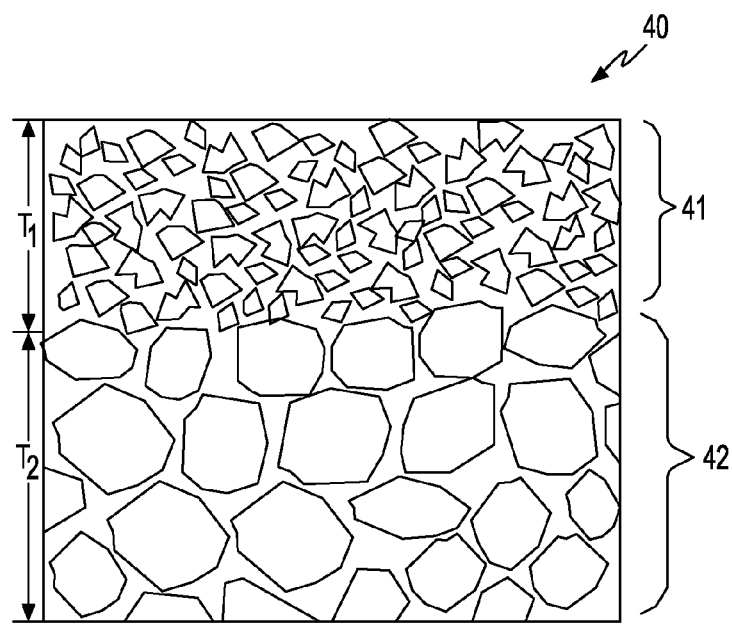
FIG. 4 is a side cross-sectional pictorial view depicting one embodiment of a micro porous membrane as employed in the separation chamber of the vapor particle separator, wherein the micro porous membrane includes at least two layers having different pore sizes, in accordance with the present disclosure.
Figure 5:
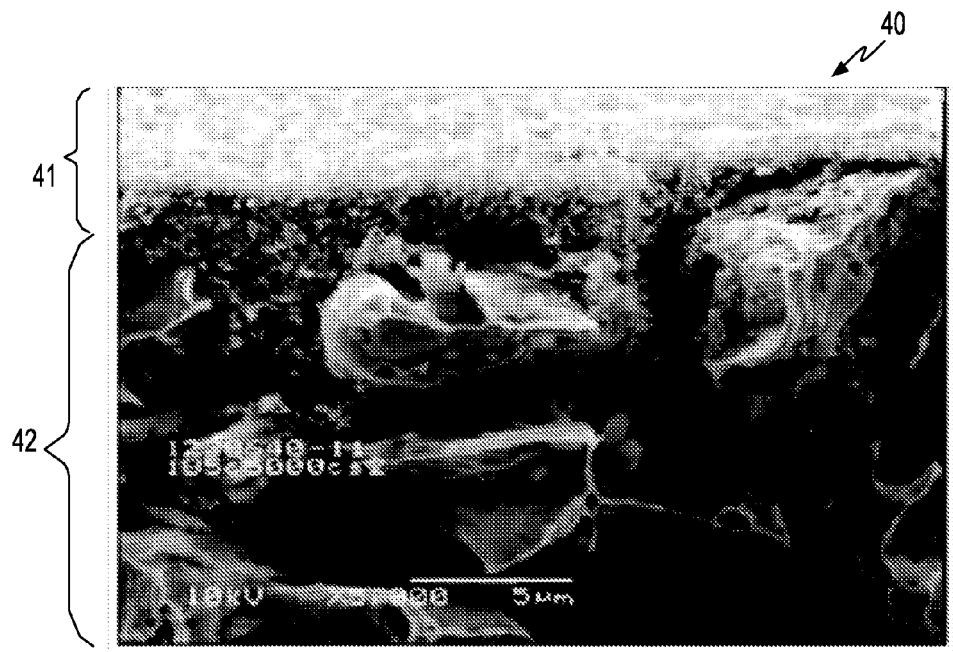
FIG. 5 is a micrograph of a micro porous membrane that includes at least two layers having different pore sizes, in accordance with one embodiment of the present disclosure.

Referring to FIGS. 4 and 5, in one embodiment, the micro porous membrane 40 is a multi-layered structure that comprises at least two layers, e.g. a first layer 41 and a second layer 42. In one embodiment, a first layer 41 of the at least two layers that provide the micro porous membrane 40 has a first thickness T1 ranging from 1 microns to 50 microns and has a first pore size ranging from 1 nm to 1,000 nm. In another embodiment, the first layer 41 has a first thickness T1 ranging from 5 microns to 20 microns and has a first pore size ranging from 5 nm to 500 nm. The first layer 41 provides the primary separation layer of the micro porous membrane 40. Typically, the desorbed gas phase molecules, i.e., desorbed vapors, from the engine combustion particles contact the first layer 41 of the micro porous membrane 40 before contacting the second layer 42 of the micro porous membrane 40. The second layer 42 of the multi-layered micro porous membrane 40 may provide structural support for the first layer 41 of the multi-layered micro porous membrane 40. In one embodiment, the second layer 42 has a second pore size ranging from 100 nm to 75,000 nm and a second thickness ranging from 10 microns to 500 microns. In another embodiment, the second layer 42 has a second pore size ranging from 500 nm to 50,000 nm and a second thickness ranging from 20 microns to 400 microns. The first and second layers 41, 42 may be composed of the same or a different material. For example, the first and second layers 41, 42 may each be composed of stainless steel, e.g., UNS# S31603 (SST-316L).

The scanning electron micrograph depicted in FIG. 5 illustrates a several micron thick multi-layered micro porous membrane 40 including a first layer 41 with individual pore sizes less than 0.5 microns deposited on a metallic backbone, i.e., second layer 42, with micro-sized pores. The backbone structures extends approximately 500 microns below the bottom of the SEM, and provides structural integrity for the micro porous membrane 40.

Referring to FIGS. 2 and 3, the micro porous membrane 40 may be formed from a sheet material into the shape of a tube, in which the ends are joined using a welding technology, such as laser welding. The micro porous membrane 40 provides the exterior wall of the particle passageway 51 and provides the interior wall of the vapor passageway 52. The exterior wall 49 of the vapor passageway 52 may be provided by a non-permeable material, such as a metal or plastic. For example, the exterior wall 49 of the vapor passageway 52 may be composed of stainless steel, such as UNS# S31603 (SST-316L). In some embodiments, the exterior wall 49 is connected to the micro porous membrane 40 at the entrance 53 to the separation chamber 50 and at the particle exit 54 of the separation chamber 50, wherein the combination of the micro porous membrane 40 and the exterior wall 49 define a chamber that provides the vapor passageway 52. In one example, the exterior wall 49 is provided by a stainless steel cylinder that is engaged to the micro porous membrane 40 by swage locked engagement.

The vapor passageway 52 may have the same length as the micro porous membrane 40. The exterior wall 49 of the vapor passageway 52 may have a cross-section across the length of the vapor passageway 52 with a substantially circular diameter or the exterior wall 49 of the vapor passageway 52 may have a multi-sided cross-section across the length of the vapor passageway 52. By substantially circular it is meant that the geometry of the cross section can be circular or oblong. Examples of multi-sided geometries for the cross-sections of the exterior wall 49 of the vapor passageway 52 include square, rectangular, pentagon and octagon shaped geometries. It is noted that the aforementioned geometries for the cross section of the exterior wall 49 of the vapor passageway 52 are provided for illustrative purposes only, and are not intended to limit the present disclosure, and any geometry that provides a passageway through the separation chamber 50 is suitable for use with the present disclosure. In some embodiments, the exterior sidewall 49 of the separation chamber 50 may be wrapped with a fiberglass based insulation.

The exit 55 (also referred to as a vapor exit 55) from the vapor passageway 52 of the separation chamber 50 is separate from the exit (also referred to as particle exit 54) of the particle passageway 51 of the separation chamber 50. In one embodiment, the vapor exit 55 is in closer proximity to the entrance 53 to the separation chamber 50 than the particle exit 54 from the separation chamber 50. Positioning the vapor exit 55 in close proximity to the entrance 53 of the separation chamber 50, reduces the chances that the desorbed gas phase molecules, i.e., desorbed vapor, can mix and re-condense with the engine combustion particles from which the gas phase molecules were desorbed in the temperature controlled chamber 45. In one embodiment, the vapor exit 55 is present through the exterior wall 49 of the vapor passageway 52 in the first ¼ length of the separation chamber 50 from the entrance to the separation chamber 50. In another embodiment, the vapor exit 55 is present through the exterior wall 49 of the vapor passageway 52 in the first ⅓ length of the separation chamber 50 from the entrance to the separation chamber 50. In yet another embodiment, the vapor exit 55 is present through the exterior wall 49 of the vapor passageway 52 in the first ½ length of the separation chamber 50 from the entrance to the separation chamber 50.

In some embodiments, the vapor exit 55 is connected to a first pump to extract the gas phase molecules, i.e., desorbed vapor, from the separation chamber 50 of the particle vapor separator (VPS) 500. In some embodiments, the gas phase molecules may be extracted through the vapor exit 55 to an instrument for analyzing the gas phase molecules that were desorbed from the engine combustion particles in the temperature controlled chamber 45. In some embodiments, the gas phase molecules, i.e., desorbed vapors, that were extracted from the separation chamber 50 through the vapor exit 55 are captured using canisters, solid phase extraction cartridges, activated carbon structures, and combinations thereof. In some embodiments, the instrument for analyzing the gas phase molecules (vapors) extracted from the separation chamber 50 may be selected from the group consisting of gas chromatograph-mass spectrometer, photon-induced ionization detector, ion-mobility spectrometer, ion-induced fluorescence, and a combination thereof.

In some embodiments, a second pump may draw the engine combustion particles through the separation chamber 50 to the particle exit 54. In some embodiments, cross flow filtration is provided by the combination of the micro porous membrane 40, the second pump that draws the engine combustion particles through the separation chamber 50 to the particle exit 54, and the first pump that evacuates the gas phase molecules, i.e., desorbed vapors, from the separation chamber 50 that have diffused through the micro porous membrane 40 into the vapor passageway 52. The combination of cross flow filtration provided by the first and second pump and the membrane separation that is provided by the micro porous membrane 40 removes the gas phase molecules from the vapor particle separator 500 that have desorbed from the engine combustion particles and prevents re-condensation of the desorbed gas phase molecules (vapors). In some embodiments, a sweeping gas, such as dry nitrogen, argon, or a combination thereof removes the gas phase molecules and the engine combustion particles from the separation chamber 50. In some embodiments, a pressure gauge port 60 may also be present through the exterior wall 49 of the vapor passageway 52 for measuring the pressure produced in the separation chamber 50 by the first and second pumps.

In one embodiment, the vapor particle separator 500 that is depicted in FIGS. 2 and 3 may be used in a method for separating desorbed vapors, i.e., gas phase molecules, from particles, i.e., engine-emitted particles, that may begin with collecting particulates of an exhaust gas from an exhaust plume of an engine. In some embodiments, a probe may be employed for collecting the particulates of the exhaust gas from an exhaust plume of an engine and for introducing the particulates of the exhaust gas to the temperature controlled chamber 45 of the vapor particle separator 500. The probe may have a tube like geometry, and may be composed of a metal, such as stainless steel. The dimensions and geometry of the probe may be based upon the type of emission sources (e.g., engine) to which the probe is applied. The engine that produces the exhaust plume from which the particulates of the exhaust gas are collected may be any internal combustion based engine. For example, the engine may be a gasoline or diesel based reciprocating engines or rotary engine. In another example, the internal combustion engine may be a turbine or a jet engine. Examples of jet engines that may produce the exhaust plume from which the particulates of the exhaust gas are collected may include turbojet, turbofan, turboshaft, ramjet and combinations thereof. In one embodiment, the particulates of the exhaust gas produced by the engine are selected from the group consisting of elemental carbon, polyaromatic hydrocarbons, trace elements, radioisotopes, and a combination thereof.

The particulates of the exhaust gas, i.e., engine combustion particles, may have a particle size with a largest axis of 1 micron or less. In different embodiments, the particulates of the exhaust gas can have a largest axis ranging 1 nm to 500 nm. For example, the particulates of the exhaust gas can have a largest axis of 2 nm, 3 nm, 4 nm, 5 nm, 10 nm, 12 nm, 15 nm, 20 nm, 25 nm, 30 nm, 40 nm, 50 nm, 100 nm, 150 nm, 200 nm, 250 nm, 300 nm, 400 nm, or 500 nm, or any range therebetween (e.g., 1-10 nm, 2-10 nm, 1-20 nm, 2-20 nm, 3-20 nm, 1-500 nm, 5-500 nm, 1-150 nm, or 5-150 nm).

In some embodiments, once entering the temperature controlled chamber 45 of the vapor particle separator 500, the particles of the exhaust gas, i.e., engine combustion particles, are heated. The temperature of the temperature controlled chamber 45 may be selected to desorb gas phase molecules, i.e., vapors, from the particulates of the exhaust gas. The desorbed gas phase molecules may have been previously condensed on the engine combustion particles as the engine combustion particles cooled while the exhaust exited the engine and contacted the ambient air. In one embodiment, the gas phase molecules, i.e., vapor, desorbed from the particulates of the exhaust gas are selected from the group consisting of linear alkane, polynuclear aromatics and a combination thereof.

The temperature of the temperature controlled chamber 45 that is selected to desorb the gas phase molecules from the particulates of the exhaust gas may range from 20° C. to 500° C. In another embodiment, the temperature of the temperature controlled chamber 45 to desorb the gas phase molecules may range from 50° C. to 400° C. In yet another embodiment, the temperature of the temperature controlled chamber 45 to desorb the gas phase molecules may range from 100° C. to 200° C.

The particles of the exhaust gas and the gas phase molecules that were desorbed from the particles of the exhaust gas in the temperature controlled chamber 45 may then be transported into the separation chamber 50 of the vapor particle separator 500. In some embodiments, the separation chamber 50 includes a particle passageway 51 to a particle exit 54 in a first direction and a vapor passageway 52 to a vapor exit 55 in a second direction, wherein the interface between the particle passageway and the vapor passageway is provided by a micro porous membrane 40. In some embodiments, the first direction of particle passageway 51 is a longitudinal direction (parallel to the length of the L2 of the separation chamber 50) through the vapor particle separator 500 and the second direction of the vapor passageway 52 is an axial direction. In some embodiments, the axial direction of the vapor passageway 52 may be substantially perpendicular to the longitudinal direction of the particle passageway 51.

In some embodiments, the method for separating vapors from particles may include applying a cross flow to the separation chamber 50 of the vapor particle separator 500 to draw the vapors, i.e., gas phase molecules, from the vapor exit 55 of the vapor particle separator 500 and to draw the particles of the exhaust gas, i.e., engine combustion particles, from the particle exit 54 of the vapor particle separator 500. In some embodiments, to provide the cross flow, a first pump may apply a first flow to the vapor exit 55 of the vapor particle passageway 52 and a second pump may apply a second flow to the particle exit 54 of the vapor particle passageway 51. In some embodiments, the application of the first flow and the second flow through the vapor exit 55 and particle exit 54 provides cross flow filtration through the separation chamber 50 of the vapor particle separator 500.

In some embodiments, a sweeping gas also be employed within the first and second pump to draw the vapors and the particles through the vapor particle separator 500. The sweeping gas is typically an inert gas, such as nitrogen or argon. Other examples of gasses that are suitable for use as the sweeping gas include particle-free air, helium, and combinations thereof. In one embodiment, the first pump that is applied to the vapor exit 55 may produce a flow rate ranging from 0.1 lpm to 5 lpm. In another embodiment, the first pump that is applied to the vapor exit 55 may produce a flow rate ranging from 1 lpm to 2 lpm. In one embodiment, the second pump that is applied to the particle exit 54 may produce a flow rate ranging from 0.1 lpm to 5 lpm. In another embodiment, the second pump that is applied to the particle exit 54 may produce a flow rate ranging from 1 lpm to 2 lpm.

In some embodiments, the vapors, i.e., gas phase molecules, that are extracted from the vapor particle separator 500 through the vapor exit 55 may be collected for further analysis. To collect the gas phase molecules that are extracted from the vapor particle separator 500 a filter, cartridge or absorption canister may be applied to the vapor exit 55. In some embodiments, the filter for collecting the gas phase molecules that are extracted from the vapor particle separator 500 is selected from the group consisting of activated carbon filters, zeolites, Tanex polymers and a combination thereof.

In some embodiments, depending on the composition and size of the engine combustion particles, as well as the composition of the gas phase molecules, i.e., vapor, that is desorbed from the gas phase molecules, the temperature of the temperature controlled chamber 45, the pore size of the micro porous membrane 40, and the flow rates applied by the first and second pumps to the vapor exit 55 and the particle exit 54 may be modified to provide for desorption of the volatile or semi volatile species, as well as the separate collection of the engine combustion particles and the desorbed species.

The following examples are provided to further illustrate the methods and structures of the present disclosure and demonstrate some advantages that arise therefrom. It is not intended that the present disclosure be limited to the specific examples described herein.

Temperature Profile of Vapor Particle Separator

Figure 6:
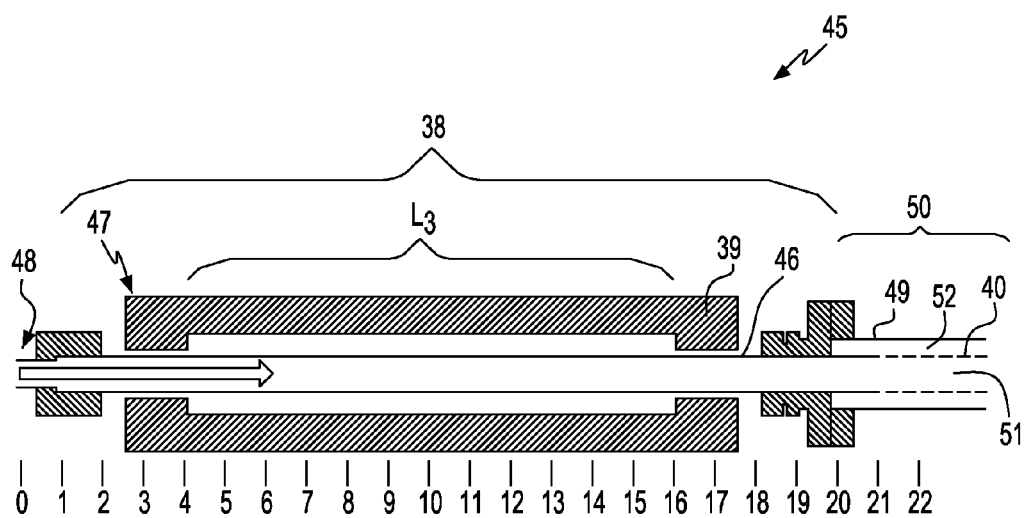
FIG. 6 is a side cross-sectional view of one embodiment of a temperature controlled chamber of a vapor particle separator, as used in accordance with one embodiment of the present disclosure.

A temperature control chamer 45 of a vapor particle system 500 was provided including a metallic tube 46 composed of 306L stainless steel, in which the metallic tube 46 had a length L3 of 30.5 cm and an inside diameter of 1.91 cm, as depicted in FIG. 6. The metallic tube 46 is immersed in a 600 W radiant heater 47 insulated by ceramic clamp-shell casing 39 and a layer of fiberglass insulation 38 on top of the ceramic clamp-shell casing 39. The heater 47 took less than 5 amps of current and control input from a proportional integral differential.

Figure 7:
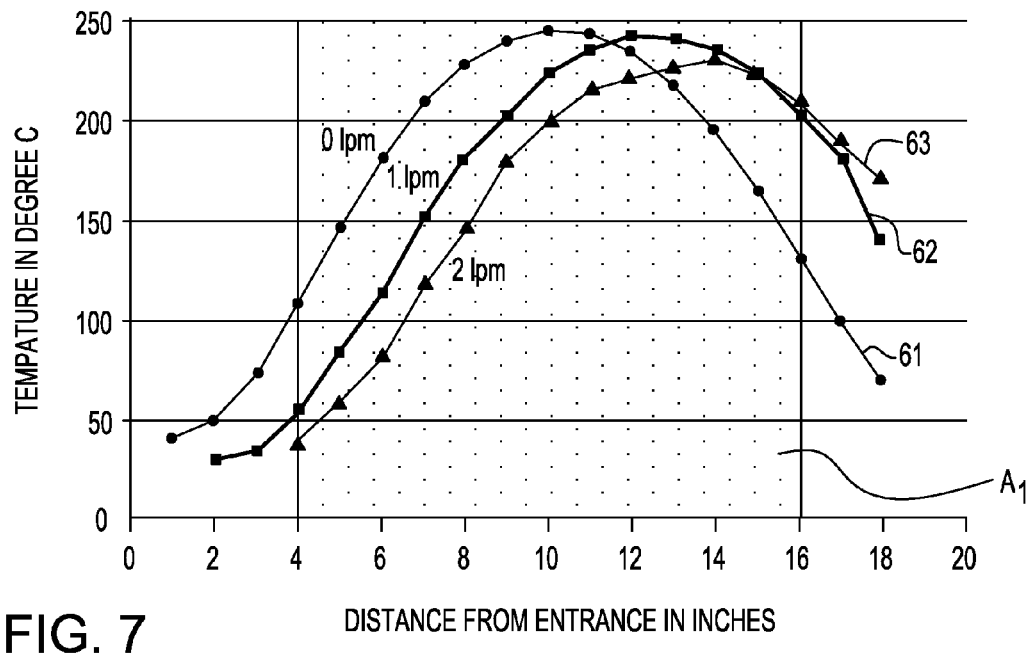
FIG. 7 is a plot of axial temperature profiles taken from the temperature controlled chamber of the vapor particle separator that is depicted in FIG. 6.

FIG. 7 is a plot of the axial temperature profiles taken from the temperature controlled chamber 45 that is depicted in FIG. 6. The axial temperature profiles for three flow rates through the temperature controlled chamber 45 are displayed in FIG. 7 for a set point temperature of 250° C. The x-axis of the plot in FIG. 7 is the distance from the sample inlet 48 to the temperature controlled chamber 45 that is depicted in FIG. 6, and the y-axis of the plot in FIG. 7 is the temperature measured at that distance from the sample inlet 48 into the temperature controlled chamber 45 in degrees Celsius. The shade area A1 depicted in FIG. 7 represents the approximate length of the active heating chamber, which was about 27.94 cm. The plot identified by reference number 61 represents a volumetric airflow rate of 0 lpm. The plot identified by reference number 62 represents a volumetric airflow rate of 1 lpm. The plot identified by reference number 63 represents a volumetric airflow rate of 2 lpm.

The three temperature distributions plotted in FIG. 7, i.e., plots 61, 62 and 63, in the axial direction of the temperature controlled chamber 45 are in a smooth symmetrical shape around the center, where the set point temperature was monitored by a K-type thermocouple, indicating the ceramic radiant heater performed well, As the sample flow through the temperature controlled chamber increased from 0 lpm (liter per minute) in plot 61, to 1 lpm in plot 62, the peak of the distribution shifted by about 5 cm to the right, and the peak temperature decrease by about 1° C. Referring to plot 63, the curve shifted further to the right when the flow was increased to 2 lpm, the peak was 10 cm from where it was at 0 lpm in plot 62, and the peak temperature decreased to around 235° C. instead of 250° C. The heating resident time was approximately 2.6 seconds estimated at the flow rate of 2 lpm. This residence time was more than sufficient to completely desorb volatiles. The axial temperature profiles at higher temperature set points are similar in trend with the volumetric airflow rates shown in FIG. 7 for 250° C. except the curve moves upward on the temperature scale.

The micro porous membrane 40 of the separation chamber 50 for vapor particle separator 500 that follows the temperature controlled chamber 45 shown in FIG. 2 was enclosed in a 5-cm diameter stainless steel tube, which provided the exterior wall 49 of the vapor passageway 52. In FIG. 6, the separation chamber 50 begins at approximately point 20. The stainless steel tube that provided the exterior wall 49 of the vapor passageway 52 was insulated by wrapping with a double-layered fiberglass blanket. The inner space between the miro porous membrane 40 and inner wall of the stainless steel tube that provides the exterior wall 49 served as the volume for the vapor passageway 52 that temporally held the escaped vapors, i.e., gas phase molecules, before they were evacuated from the vapor particle separator by an extraction pump, which left no opportunity for the vapor, i.e., gas phase molecules, to re-enter the micro porous membrane 40 and condense on the engine combustion particles contained within the particle passageway 51. The temperature of the vapor passageway of the separation chamber 50 at the location labeled 21 in FIG. 6 was measured at 150° C. when the set point temperature was at 250° C. and the volumetric airflow rate was set at 2 lpm. It is unlikely that the vapors, i.e., pas phase molecules, can condense back to engine combustion particles at this point, i.e., location 21, or further into the separation chamber 50. The temperature at the exit end, e.g., particle exit 54 depicted in FIG. 2, of the separation chamber 50 was 50° C. or less.

Particle Loss Through Vapor Particle Separator at Room Temperature

Generation of Test Particles:

The vapor particle separator (VPS) instrument was evaluated using synthetic particles. These synthetic particles included (1) a nonvolatile material sodium chloride (NaCl) and (2) a semi-volatile material dioctyl phthalate (DOP). The nonvolatile materials had a vapor pressure less than $10^{-4}$ mmHg at room temperature (20° C. to 25° C.). Research-grade reagents of sodium chloride (NaCl), dioctyl phthalate (DOP), and ethanol were used without further purification. Deionized water of 18 M was used in the preparation of all stock solutions. The sodium chloride (NaCl) stock was prepared as 0.01% w/w (weight-to-weight) solution, while dioctyl phthalate (DOP) was prepared as 0.01% v/v (volume-to-volume) but the solution was 50/50 water and alcohol mixture to help drying the test particles.

Figure 8:
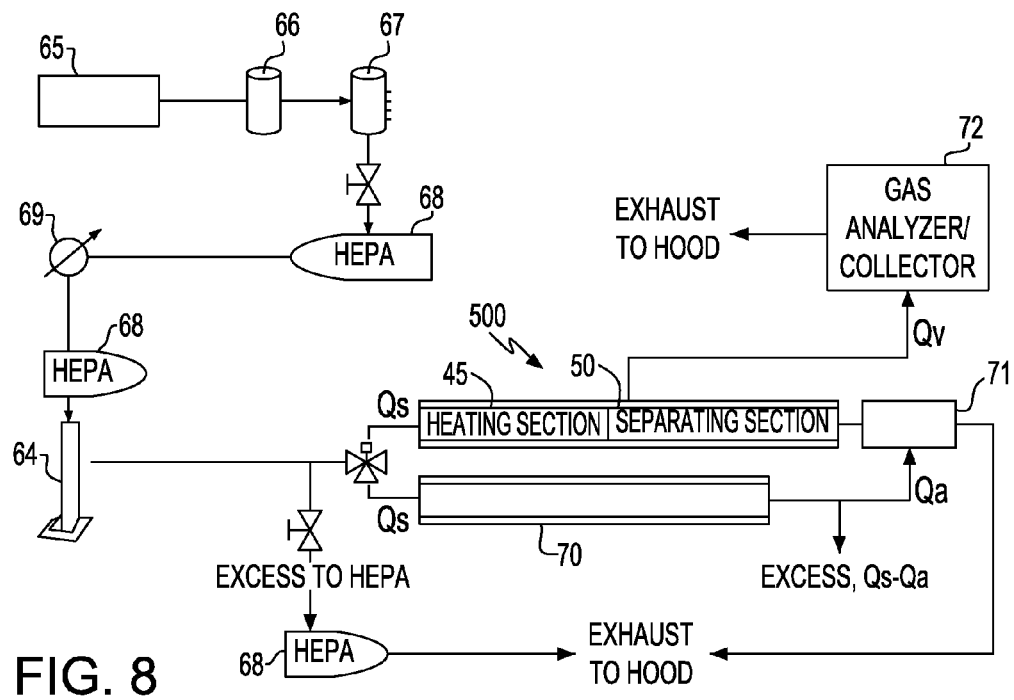
FIG. 8 is schematic view depicting the apparatus for separating gas phase molecules (also referred to as vapors) from engine combustion particulates, in accordance with one embodiment of the present disclosure.

Experimental Set Up:

The experimental apparatus that was employed to determine particle loss at room temperature is depicted in FIG. 8, which includes a vapor particle separator 500 as described with reference to FIGS. 2, 3 and 6. An atomizer 64 (TSI Model 3076) was used to generate polydisperse test particles using building supply air 65. The atomizer 64 included a first stock bottle containing a prepared solution, and a second bottle for holding the non-atomized solution that was recycled back. The building-supply air 65 was passed through a dessicant filter 66, an activated carbon canister 67 and at least one high-efficiency particulate air (HEPA) filter 68 to provide particle-free air for driving the atomization. At least one pressure regulator 69 was positioned before the atomizer 64 to control the flow rate of the particle-free air to the atomizer 64.

The particles produced by the atomizer 64 entered either the vapor particle separator (VPS) 500 or a stainless steel bypass tube 70. The vapor particle separator 500 included a temperature controlled chamber 45, as described above with reference to FIG. 6. The separation chamber 50 included a micro porous membrane 40, as described with reference to FIGS. 2 and 3. In the experimental apparatus, the micro porous membrane 40 was a double-layer metallic microporous membrane tube having an internal diameter (ID) about 1.91 cm and 25.4 cm long. The nominal pore size of the micro porous membrane was approximately 0.4 μm and the thickness was about 420 μm. The micro porous membrane tube was swagelok sealed, and was enclosed inside a stainless steel cylinder. The micro porous membrane 40 was made of 306L stainless steel that could resist pressures greater than 400 kPa and backpressures greater than 10 kPa. The exterior wall 49 of the vapor passageway of the separation chamber 50 was provided by a stainless steel cylindrical enclosure that was insulated using fiberglass insulation material. The bypass tube 70 was used as the reference in the calculations of particle transmission efficiency through the vapor particle separator 500. The bypass tube 70 was dimensionally identical to that of the micro porous membrane 40 with the exception that the wall of the bypass tube 70 was solid and had no membrane.

The sampling flow rate Qs through the vapor particle separator 500 was operated at 2.0 lpm. Off the total 2.0 lpm flow, 1.5 lpm was through the particle passageway 51 of the separation chamber 50 of the vapor particle separator 500 where there was a flow rate Qa of 0.5 lpm that was sampled by a scanning mobility particle sizer (SMPS)(TSI Model 3096N) 71 that was equipped with a nano-differential mobility analysis (DMA) (TSI Model 3085) and an ultrafine condensation particle counter (UCPC) (TSI Model 3025A) for measurement of the particle size distribution.

Gas phase molecule, i.e., desorbed vapor, removal was performed by using a pump at a rate Qv of 0.5 lpm in the normal direction to the flow streamline through the micro porous membrane 40. The pump pulled the gas phase molecules, i.e., vapor, to be collected in a gas analyzer/collector 72. This configuration was similar to cross-flow filtration, in which vapor, i.e., gas phase molecules, or filtrate was permeated through the micro porous membrane while engine combustion particles were passing in parallel to the surface of the micro porous membrane 40 through the particle passageway. The radial velocity of the flow was insignificant compared to the axial flow velocity in this configuration. Thus, in the vapor particle separator 500, the micro porous membrane 40 acts as an effective barrier to the engine combustion particles, preventing loss of the engine combustion particles through the micro porous membrane 40 in the counter-flow design, which preserves the true total particle count exiting the vapor particle separator 500 to a particle instrument, such as SMPS 71.

Particle Transmission Efficiency:

Loss of particles, i.e., engine combustion particles, particularly those less than 100 nm in diameter, such as those commonly seen in aircraft engine emissions is a concern for particle measurement through a vapor particle separator whether the particles are volatile or non-volatile. Particles as small as the engine combustion particles do not have significant inertia to be affected by aerodynamic forces (e.g., impaction). Ignoring other forces, such as electrostatic and image forces, the loss mechanisms for engine combustion particles in a tube, such as the geometry provided by the micro porous membrane 40, are diffusion and thermophoretic, which are strongly dependent on temperature and weakly dependent on the geometry of the transport tube.

To determine the particle transmission loss through the vapor particle separator 500, 0.01 wt % dioctyl phthalate (DOP) was flowed through the vapor particle separator 500 and the bypass tube 70 using the flow rates described in the experimental set up. By comparing the size distributions of particles, i.e., dioctyl phthalate (DOP), that were obtained at the outlet 54 of the vapor particle separator 500 and that of the bypass tube 70 of the same length with the temperature controlled chamber 45 of the vapor particle separator 500 turned off, it was possible to evaluate the particle transmission loss of the instrument. Because the temperature controlled chamber 45 of the vapor particle separator 500 was turned off, the test was conducted at room temperature (25° C.). Particle transmission is an important parameter of the instrument performance. An ideal particle instrument would have a 100% transmission with no loss of particles in the instrument.

Figure 9:
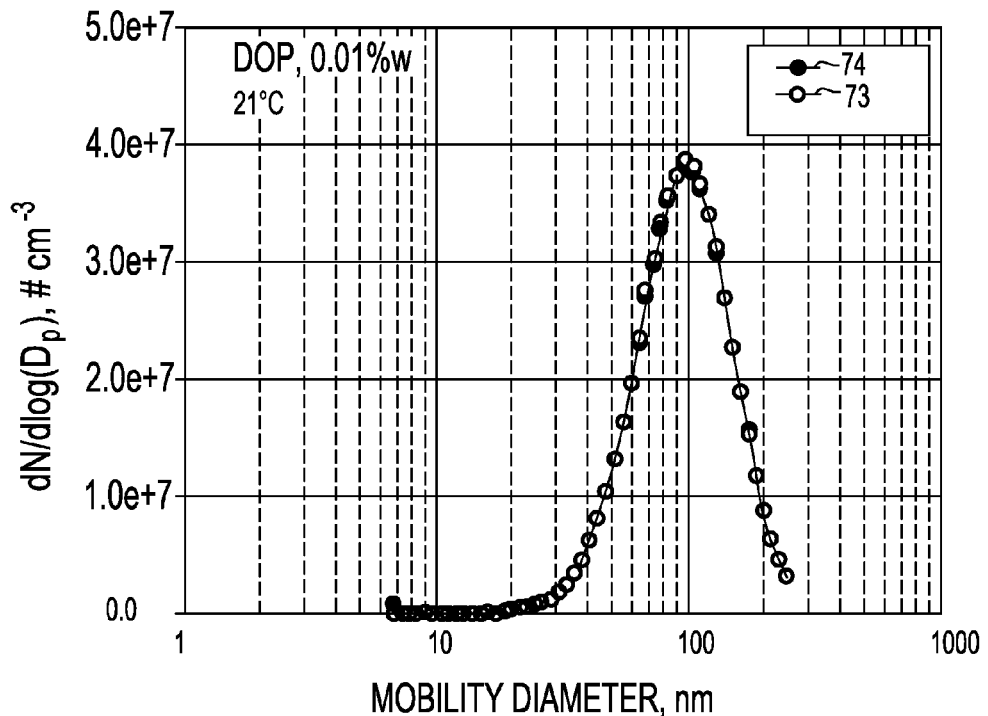
FIG. 9 is a plot of particle size distribution of dioctyl phthalate (DOP) particles drawn through the vapor particle separator of the apparatus depicted in FIG. 8 in comparison to particle size distribution of dioctyl phthalate (DOP) particles drawn the bypass tube of the apparatus depicted in FIG. 8.

Test results for the particles of the dioctyl phthalate (DOP) that was flowed through the vapor particle separator 500 and the bypass tube 70 are depicted in FIG. 9. FIG. 9 is a plot of the particle size distributions of dioctyl phthalate (DOP) particles through the vapor particle separator 500 and the bypass tube 70, in which the y-axis is the chromatograph peak height of flame ionization detector response (no unit) and the x-axis is the mobility. Data line 73 represents the particles of dioctyl phthalate (DOP) through the vapor particle separator 500 and data line 74 represents the particles of dioctyl phthalate (DOP) through the bypass tube 70. The data plotted in FIG. 9 illustrated that the particle transmission efficiency of dioctyl phthalate (DOP) particles through the vapor particle separator 500 is virtually identical to that of the bypass tube 70 for all materials tested at the room temperature (no heating applied). The loss of dioctyl phthalate (DOP) particles through the vapor particle separator 500 was minute, i.e., below the detectable limit of the scanning mobility particle sizer (SMPS)(TSI Model 3096N) 71. For the purposes of the experimentation, there was practically no loss of dioctyl phthalate (DOP) particles in the vapor particle separator 500.

Similar tests were also been done using a number of materials that include sodium chloride, sucrose, nickel chloride, and ammonium sulfate. Similar results were obtained and all show that the transmission loss through the vapor particle separator 500 was minimum, e.g., less than 1%.

Effect of Temperature on Volatile and Non-Volatile Particle Loss through Vapor Particle Separator Generation of Test Particles:

To investigate the thermal separation efficiency of the vapor particle separator and heating effect on particles, such as engine combustion particles, monodisperse particles were employed rather than polydisperse particles. Monodisperse particles are those that in theory have substantially one size. In practice, the geometric standard deviation of a particle size distribution less than or equal to 1.2 is consider monodisperse, assuming the size distribution follows a lognormal distribution. In practice, tandem differential mobility analysis (TDMA) was demonstrated for the production of monodisperse particles of equivalent mobility diameter. A nano-DMA was used as the size selector to extract particles from the broadband atomizer-generated particle population. (CAN WE ELABORATE ON THIS—WE SHOULD NOT CROSS REFERENCE). The particle compositions for the non-volatile particle population was sodium chloride (NaCl) having a particle size of 17 nm, 28 nm and 55 nm. The particle composition for the volatile particle population was dioctyl phthalate (DOP) having a particle size of 30 nm, 50 nm and 80 nm.

Experimental Set Up:

FIG. 10 depicts the experimental set up for studying the effect of temperature on particle volatility obtained by the vapor particle separator 500. An aerosol including particles, such as volatile particles, e.g., dioctyl phthalate (DOP), or non-volatile particles, e.g., sodium chloride (NaCl), that was produced by an atomizer 64 was introduced to a mixing chamber 76. The particles are described above in the section titled "generator of test particles". From the mixing chamber 76 the particles, such as volatile particles, e.g., dioctyl phthalate (DOP), or non-volatile particles, e.g., sodium chloride (NaCl), were introduced to a first electric classifier 78. The electric classifier was used as a size selector. The size-selected particles, e.g., dioctyl phthalate (DOP), or non-volatile particles, e.g., sodium chloride (NaCl), were then sent into the vapor particle separator 500 where the particles are treated by heat. The vapor particle separator 500 was the same as the vapor particle separator used in the experimental apparatus for the measurements of particle less through the vapor particle separator at room temperature. A pump 79 was connected to the particle exit end of the vapor particle separator 500. Following exit of the particles, such as volatile particles, e.g., dioctyl phthalate (DOP), or non-volatile particles, e.g., sodium chloride (NaCl), from the vapor particles separator 500, the particles were analyzed by a second electric classifier 80. The second electric classifier 80 was used to provide measurement of particle size distribution after the vapor particle separator. The particles exiting the particle exit of the vapor particle separator were measured by a scanning mobility particle sizer (SMPS)(TSI Model 3096N) 75 that was equipped with a long DMA and an ultrafine condensation particle counter (UCPC), while the vapors leaving through the vapor exit of the vapor particle separator 500 are collected by charcoal or solid phase adsorption (not shown). A gas analyzer (not shown) can also be connected to the vapor exit for direct on-line gas analysis.

Effect of Temperature on Non-Volatile Particle Population:

Sodium chloride (NaCl) is nonvolatile in the temperature range of 21° C. to 400° C. The melting point of sodium chloride (NaCl) is 801° C. and the boiling point is 1413° C. The vapor pressure is on the order of 10-16 mmHg. A flow of sodium chloride (NaCl) particles was run through the experimental set up including the vapor particle separator 500 that is depicted in FIG. 10.

The particle size distributions reflecting the thermal behavior of the monodisperse sodium chloride (NaCl) particles of three selected sizes (17, 28, and 55 nm) are shown in FIGS. 11A, 11B and 11C. FIG. 11A is a plot of the particle size distribution of sodium chloride (NaCl) particles at 0.1 wt % having a particle size of 17 nm in response to five heating temperatures of the temperature controlled chamber 45 of the vapor particle separator 500. The five temperatures included room temperature, i.e., 21° C., 100° C., 200° C., 300° C. and 400° C. FIG. 11B is a plot of the particle size distribution of sodium chloride (NaCl) particles at 0.1 wt % having a particle size of 28 nm in response to the same five heating temperatures that provided the data plots in FIG. 11A. FIG. 11C is a plot of the particle size distribution of sodium chloride (NaCl) particles at 0.1 wt % having a particle size of 55 nm in response to the same five heating temperatures that provided the data plots in FIG. 11A.

The geometric standard deviation (σg) of each of the three selected particle sizes for the sodium chloride (NaCl) particles at 21° C. is less than 1.1 indicating the selected particles are practically one size. Referring to FIG. 11A, as the heating temperature (T) increased from 21° C. (the room temperature) to 100° C., the peak mobility diameter remained unchanged. The peak height at 17 nm reduced by 25% as the heating temperature (T) was increased from 21° C. to 100° C. indicating a loss of particles. Sodium chloride (NaCl) is non-volatile under these two temperature conditions. To determine that the loss of sodium chloride (NaCl) particles did not result from transfer to the micro porous membrane 40 of the vapor particle separator 500, the micro porous membrane 40 was rinsed and tested using a conductivity meter (VWR Scientific Model 2052) to measure the change of conductivity on the rinsed solution and found the conductivity remained constant indicating there was no detectable amount of salt (i.e., NaCl) deposited on the micro porous membrane. In view of this experimentation, it was determined that the decrease in the particle count from room temperature 21° C. to 100° C. plotted in FIG. 11A was because of the thermal effects.

Volatilization of the 17-nm sodium chloride (NaCl) particles appeared to occur at a temperature that was less than expected based upon the melting (801° C.) and boiling temperatures (1401° C.) of the sodium chloride (NaCl) salt grains. Referring to plot 11A, as the temperature was further increased further from 100° C. to 200° C., 300° C. and 400° C., the peak size location of sodium chloride (NaCl) particles remained stationary at approximately 17 nm, but the peak height, i.e., particle count, decreased further as the heating temperature was increased indicating that progressively more sodium chloride (NaCl) particles vaporized, as the temperature was increased. The decrease in the peak height, i.e., particle count, appears to accelerate from 200° C. to 300° C. and to 400° C. as compared to those at the lower temperatures tested.

The thermal behavior appears to indicate that atoms are located at the surface of nanoscale sized non-volatile sodium chloride (NaCl) particles, which escape from the main crystal structure easier than those from a larger particle, which led to a lower melting point for nano-NaCl particles. The thermodynamic behavior of the 28 nm sodium chloride (NaCl) particles (plotted in FIG. 11B) and the 55-nm sodium chloride (NaCl) particles (plotted in FIG. 11C) at each of the operated temperatures appears to be similar to that of the 17 nm sodium chloride (NaCl) particles (plotted in FIG. 11C). The stepwise change of particle number concentration at the selected 28 nm or 55 nm sodium chloride (NaCl) particles peak is milder in the temperature range from 21° C. to 300° C. than that for the 17 nm sodium chloride (NaCl) particles supporting that the 17 nm sodium chloride (NaCl) particles vaporized more readily than the larger sodium chloride (NaCl) particles, e.g., 28 nm and 55 nm sodium chloride (NaCl) particles. The rate of loss accelerated at the temperature from 300° C. to 400° C. Thus, for non-volatile sodium chloride (NaCl) particles, increase of the heating temperature to a sufficiently high level can vaporize small particles in the vapor particle separator causing reduction in the number of particles as reflected in the SMPS spectra. Since the vapor particle separator allows one to operate on evacuation of vapor desorbed from the sodium chloride (NaCl) particles through the micro porous membrane, the vapor particle separator 500 reduces the potential for forming new particles in the core flow. As a result, the peak location (i.e., the size) of the sodium chloride (NaCl) particles did not change in different heating temperatures, but the number of particles were reduced.

Figure 10:
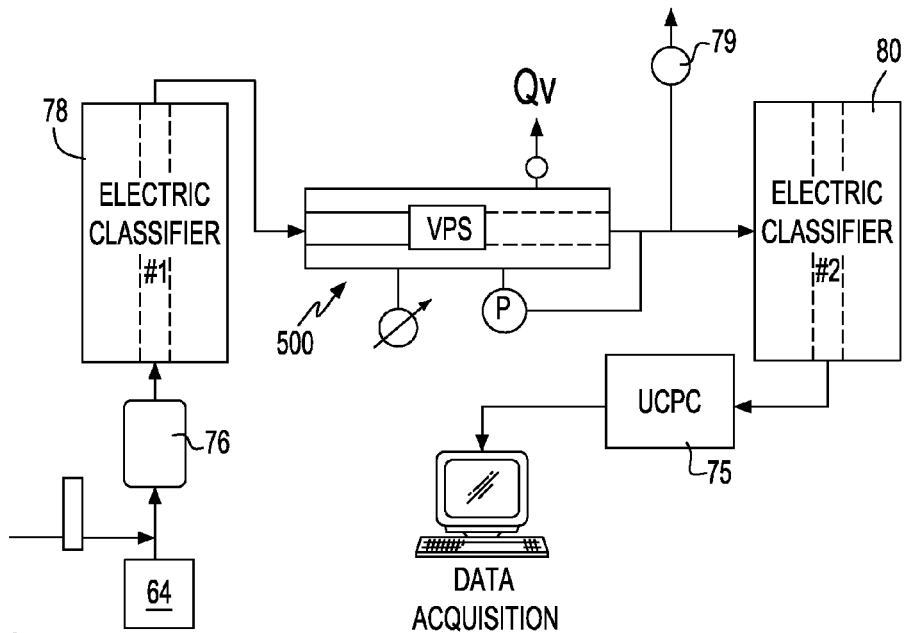
FIG. 10 depicts a schematic view of an apparatus for studying the effect of temperature on the volatility of particles that are applied to a vapor particle separator, in accordance with one embodiment of the present disclosure.
Figure 11A:
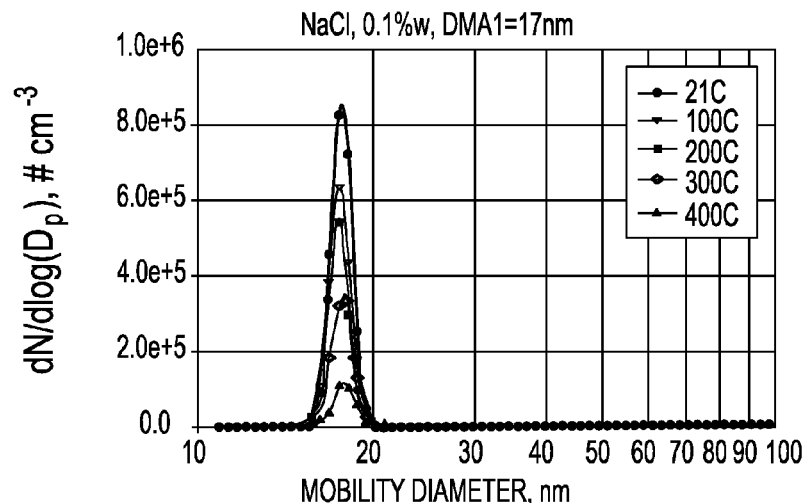
FIGS. 11A-11C are plots of the particle size distribution measured from the vapor particle separator of sodium chloride (NaCl) particles having a particle size of 17 nm, 28 nm and 55 nm in response to heating temperatures ranging from 21° C. to 400° C., in accordance with some embodiments of the present disclosure.
Figure 11B:
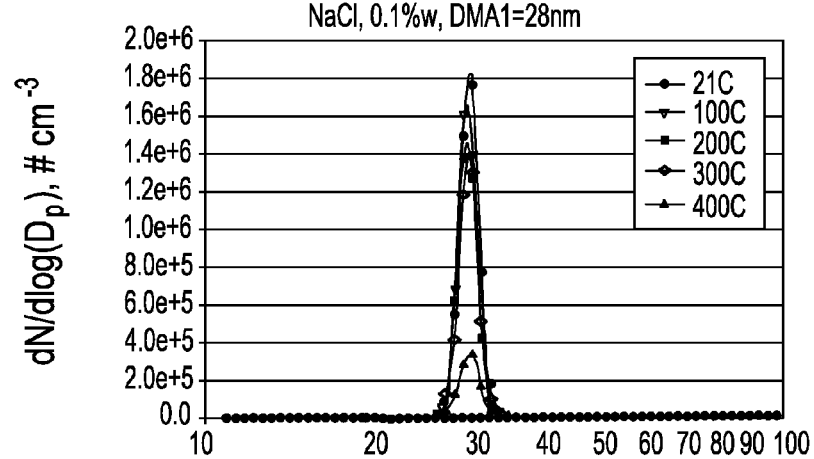
Figure 11C:
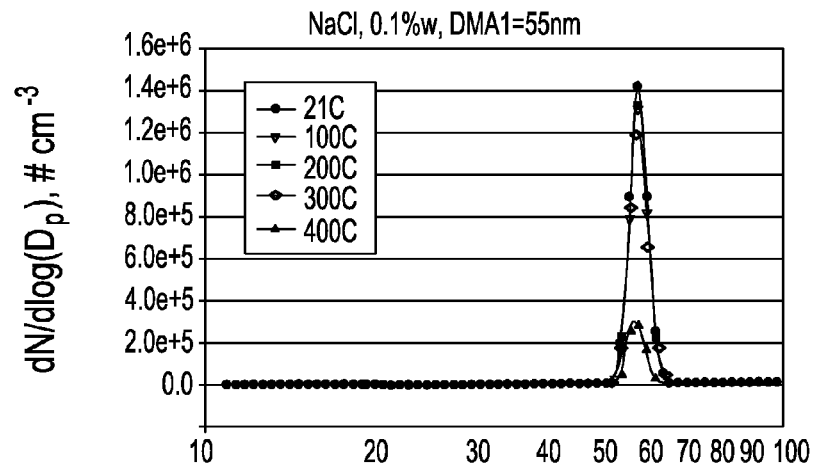

Effect of Temperature on Non-Volatile Particle Population:

When monodisperse dioctyl phthalate (DOP) particles were applied the vapor particle separator 500 through the experimental apparatus depicted in FIG. 10, the particle population dynamics in response to heating temperature was more versatile that of the sodium chloride (NaCl) particles. The melting point of dioctyl phthalate (DOP) is −50° C. (223 K) and boiling point is 385° C. (658 K). The vapor pressure at the room temperature (21° C.) was on the order of $6\times10^{-8}$ mmHg, $5\times10^{-6}$ at 50° C. and $1.4\times10^{-3}$ at 100° C. A flow of dioctyl phthalate (DOP) particles was run through the experimental set up including the vapor particle separator 500 that is depicted in FIG. 10.

Figure 12A:
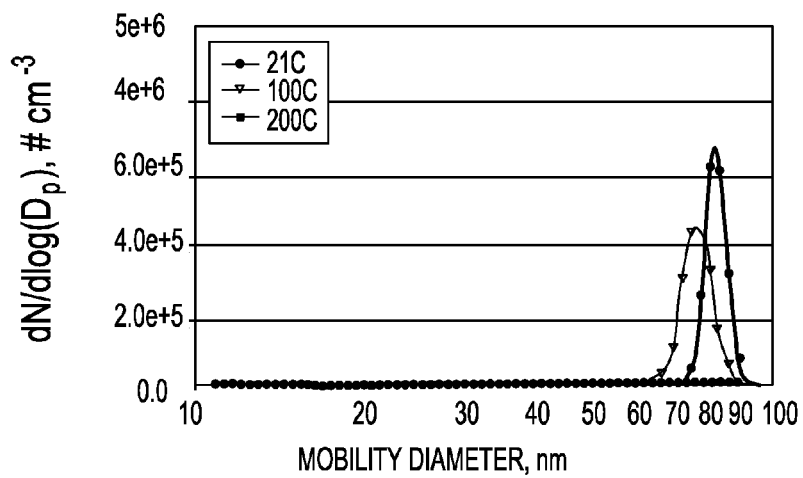
FIGS. 12A-12C are plots of dioctyl phthalate (DOP) particles having a particle size of 80 nm, 30 nm and 50 nm in response to heating temperatures ranging from 21° C. to 100° C., in accordance with some embodiments of the present disclosure.
Figure 12B:
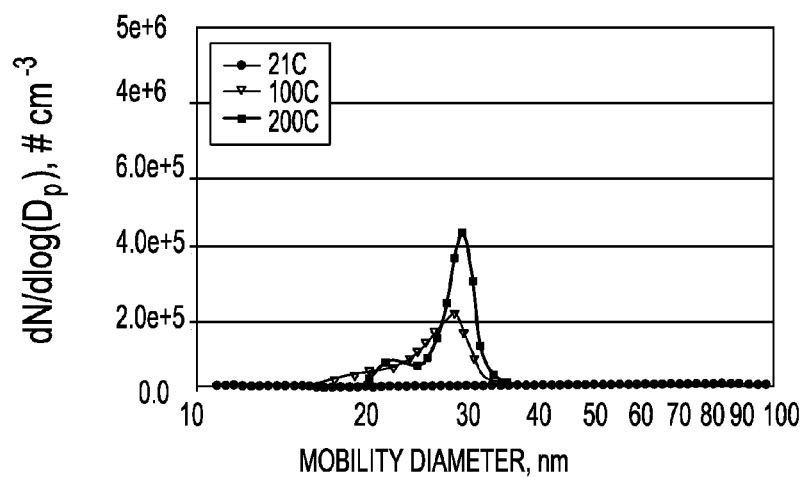
Figure 12C:
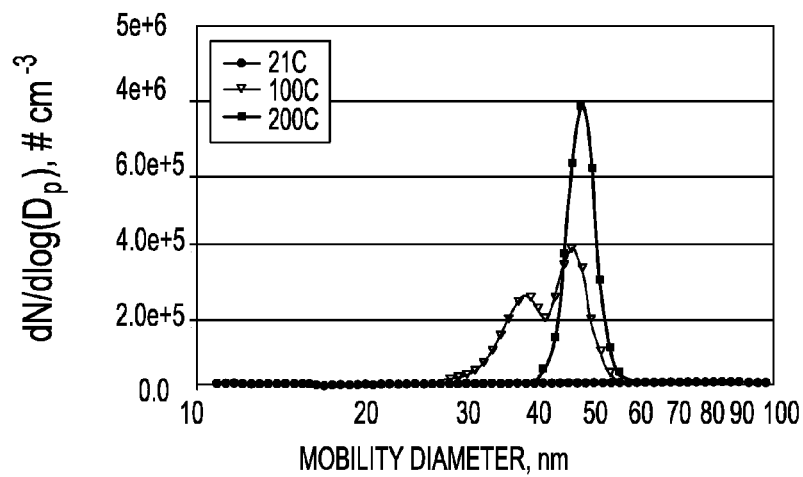

The results for the particle size distribution of dioctyl phthalate (DOP) that was flowed through the vapor particle separator 500 of the experimental apparatus depicted in FIG. 10 are plotted in FIGS. 12A-12C. FIG. 12A is a plot of the particle size distribution of dioctyl phthalate (DOP) particles having a particle size of 80 nm in response to three heating temperatures of the temperature controlled chamber 45 of the vapor particle separator 500. The three temperatures included room temperature, i.e., 21° C., 50° C. and 100° C. FIG. 12B is a plot of the particle size distribution of dioctyl phthalate (DOP) particles having a particle size of 30 nm in response to the same three heating temperatures that provided the data plots in FIG. 12A. FIG. 12C is a plot of the particle size distribution of dioctyl phthalate (DOP) particles having a particle size of 50 nm in response to the same three heating temperatures that provided the data plots in FIG. 12A.

Referring to FIG. 12B, the particle size distribution of the 30 nm dioctyl phthalate (DOP) particles at 21° C. appeared to be bimodal with a small hump found at approximately 20 nm. As the temperature of the temperature controlled chamber of the vapor particle separator was increased to 50° C., the decrease in the heat of the main peak (at approximately 30 nm) for the 30 nm dioctyl phthalate (DOP) particles at 21° C. was dramatic as compared to the 28 nm particles of sodium chloride (NaCl). The decrease was on the order of 50%. The 30 nm dioctyl phthalate (DOP) particles vaporized when the temperature of the temperature controlled chamber of the vapor particle separator was increased to 100° C.

Referring to FIG. 12C, similar behavior in the particle size distribution in response to changes in temperature was exhibited by the 50 nm dioctyl phthalate (DOP) particles. The small hump in the particle size distribution of the 30 nm dioctyl phthalate (DOP) particles at 21° C. (depicted in FIG. 12B) was not displayed in the plot in FIG. 12C of the data set provided by the 50 nm dioctyl phthalate (DOP) particles at the same temperature, because the main peak depicted in FIG. 12C was visually larger than the small hump. The production of particles smaller than the main peak size was obvious and could be identified in FIG. 12C in the bimodal distribution. The peak size of the large mode is slightly smaller than 50 nm of the DMA1 selected size, while the peak size of the second mode is around 38 nm. The 38 nm particles appeared to have been generated by the evaporation of the dioctyl phthalate (DOP) molecules from the larger dioctyl phthalate (DOP) particles during the heating process in the temperature controlled chamber 45 of the vapor particle separator 500.

Referring to FIG. 12A, the shift in the main dioctyl phthalate (DOP) particle size becomes more pronounced with the 80 nm dioctyl phthalate (DOP) particles. As the temperature of the temperature controlled chamber 45 of the vapor particle separator 500 was increased from 21° C. to 50° C., the peak height decreased by approximately 30% and the peak location shifted to the left with a size decrease of about 7 nm. There was no secondary hump produced by the data set for the 80 nm dioctyl phthalate (DOP) particles plotted in FIG. 12A that would indicate a bimodal particle size distribution, as was found in the data set for 30 nm dioctyl phthalate (DOP) particles plotted in FIG. 12B or the data set for 50 nm dioctyl phthalate (DOP) particles plotted in FIG. 12C. The 80 nm dioctyl phthalate (DOP) particles completely vaporized when the temperature of the temperature controlled chamber 45 of the vapor particle separator 500 was increased to 100° C.

Rate of Thermal Removal of Nanoparticles.

Figure 13:
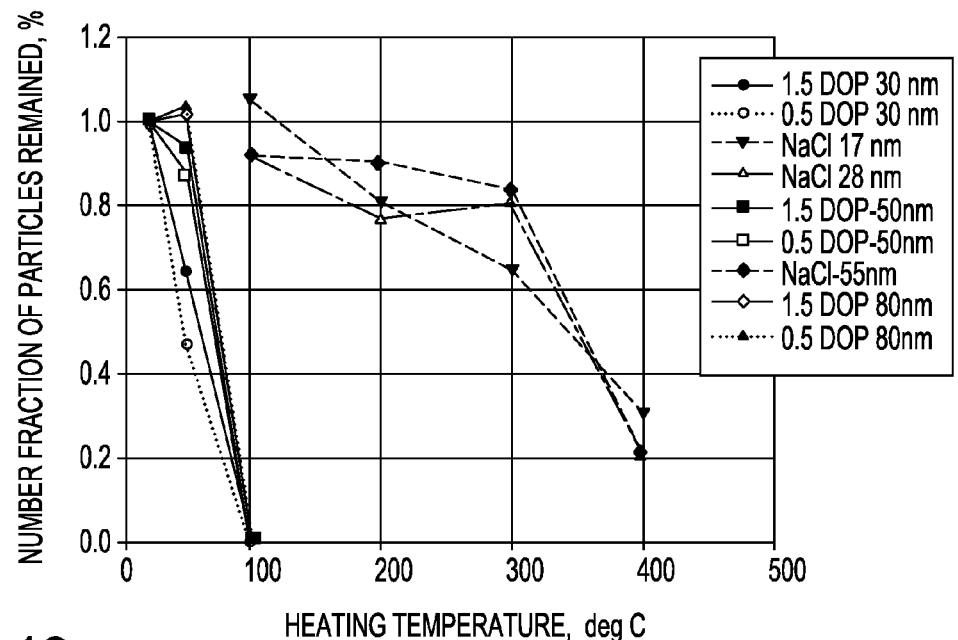
FIG. 13 is a plot of number fractions of dioctyl phthalate (DOP) and sodium chloride (NaCl) obtained from one embodiment of a vapor particle separator after heat treatment, in accordance with the present disclosure.
Figure 14:
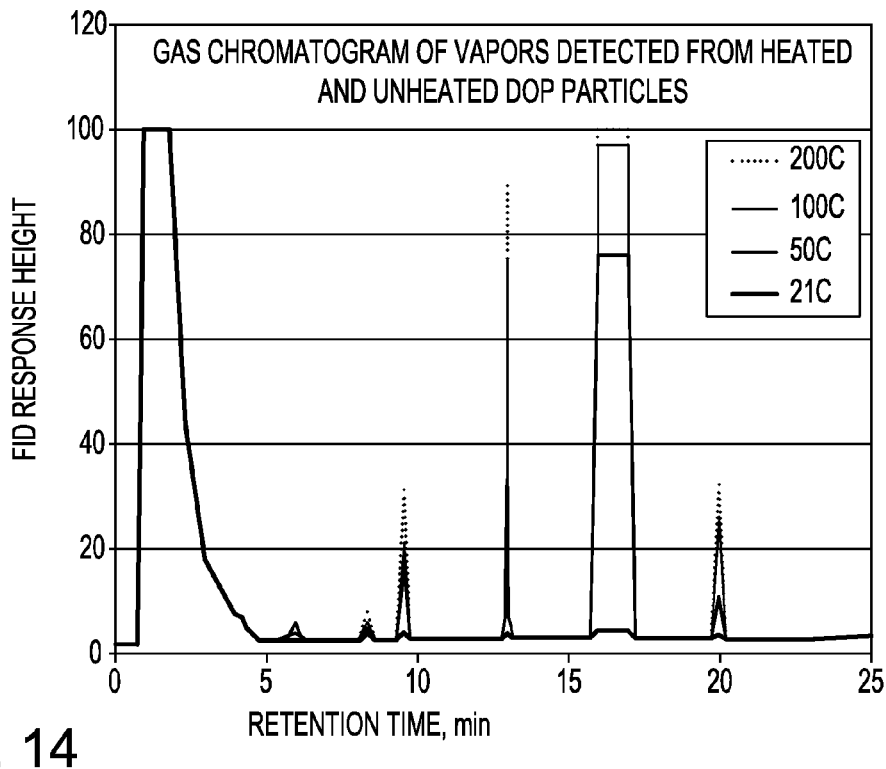
FIG. 14 depicts gas chromatograms of vapors extracted from a vapor particle separator that contained particles from an engine exhaust, in accordance with one embodiment of the present disclosure.

FIG. 13 illustrates the thermal effects on the evaporation of nanoscale particles passed through the vapor particle separator 500. The number fraction of particles remained after the thermal evaporation step is plotted as a function of heating temperature in FIG. 13 for two selected nanoparticles, i.e., sodium chloride (NaCl) and dioctyl phthalate (DOP). The nanoparticles were thermally removed (i.e., evaporated) as the heating temperature in the temperature controlled chamber 45 of the vapor particle separator 500 increased. The removal rate as a function of temperature was strongly dependent on the material (e.g., sodium chloride (NaCl) particles require significantly higher temperature to vaporize than dioctyl phthalate (DOP) particles) and the size of the nanoparticles (e.g., 80 nm particles require higher temperature to be completely vaporized than 17 nm one at the same vapor particle separator operating condition).

As illustrated by differences in the removal curve shown in FIG. 13, the approach of using solely heating temperature to categorize particles as volatile or not volatile can be questionable. The term "volatile engine particles" is size and composition dependent, and typically cannot be described by a single operational parameter, e.g., temperature. The 30 nm dioctyl phthalate (DOP) particles vaporized faster than the 80 nm dioctyl phthalate (DOP) particles. For the curves in this dioctyl phthalate (DOP) group in FIG. 13, there was evidence of a slight difference in removal rate due to the difference in the flow rate Qv through the micro porous membrane 40, e.g., the data produced by the flow rate Qv of 1.5 lpm verses the data produced by the flow rate Qv of 0.5 lpm. The impact of the flow rate Qv through the micro porous membrane 40 extracted through the vapor exit 55 is slightly higher for the smaller dioctyl phthalate (DOP) particles, e.g., 30 nm dioctyl phthalate (DOP) particles, than for the larger dioctyl phthalate (DOP) particles, e.g., 80 nm dioctyl phthalate (DOP) particles.

Similar observations were also found for sodium chloride (NaCl) particles. The thermal removal of the 17 nm sodium chloride (NaCl) particles was faster than for the 55 nm particles of sodium chloride (NaCl). It was also observed that there appeared to be an area where the removal of particles remained reasonably constant as a function of temperature. For example, the removal of particles remained reasonably constant as a function of temperature within the range of temperature of 100° C. to 300° C. for 28 nm or greater sodium chloride (NaCl) particles and 20° C. to 50° C. for dioctyl phthalate (DOP) particles greater than 50 nm. Response of the smallest sodium chloride (NaCl) nanoparticles to the heating temperature was in contrasting to that of the larger particles of sodium chloride (NaCl). Given the same material, particles will evaporate faster as their sizes become smaller. The evaporation rate can have a low threshold limit below that the nanoparticles would completely vaporized instantly upon entering the controlled temperature chamber 45 of the vapor particle separator 500.

The non-volatile sodium chloride (NaCl) particles exhibited a transient behavior responding to heat that is different from the volatile dioctyl phthalate (DOP) particles. The non-volatile particles respond to the increased temperature by losing particles through the vaporization route, the peak size of the non-volatile particles did not change with respect to the increased temperature. A semi-volatile material, such as dioctyl phthalate (DOP), also lost particles (i.e., number concentration) through vaporization in response to the increased temperature, but it also produced small particles. The particle loss/removal as a function of temperature appeared to be material and size dependent. The experimental results demonstrated that the vapor particle separator 500 of the experimental setup described with reference to FIG. 10 is a high efficiency vapor-particle separator.

Measure of Vapor through the Membrane:

One objection of the design in the vapor particle separator 500 including the micro porous membrane 40 was to provide a means not only enabling high-efficiency separation of gas phase molecules, e.g. desorbed vapors, from particles, such as engine combustion particles, but also the extraction and subsequent analysis of gas phase molecules, i.e., desorbed vapors. FIG. 14 demonstrates the analysis of the separated gas phase molecules, e.g. desorbed vapor, that was extracted from vapor particle separator 500. The plot in FIG. 14 is the gas chromographs of the vapors, i.e., gas phase molecules, desorbed from dioctyl phthalate (DOP) particles in four temperature conditions, i.e., 21° C., 50° C., 100° C. and 200° C. As the temperature was increased, the peak height increased in response to the increased loss of particles to the vapor phase.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A vapor particle separator comprising:

a temperature controlled chamber for desorbing vapors from the particulates of an exhaust gas that enters the vapor particle separator through the temperature controlled chamber; and a separation chamber including a micro porous membrane for providing an interface between at least one particle passageway and at least one vapor passageway through the separation chamber, the particle passageway extends from an entrance to the separation chamber to a particle exit of the separation chamber, the vapor passageway extends from the micro-porous membrane to a vapor exit from the separation chamber that is separate from the particle exit from the separation chamber, wherein the micro porous membrane has a pore size that allows for diffusion of the vapors from the particle passageway through the micro porous membrane to the vapor passageway, wherein the particles having a lower diffusivity than the vapors are obstructed from entering the vapor passageway.

2. The vapor particle separator of claim 1, wherein the temperature controlled chamber comprises a metallic tube that is positioned within a heater.

3. The vapor particle separator of claim 2, wherein the metallic tube is composed of a metal selected from the group consisting of stainless steel, aluminum, copper, titanium, zirconium or combinations thereof.

4. The vapor particle separator of claim 2, wherein the metallic tube provides the sample inlet to the vapor particle separator and continuously extends to the entrance chamber of the vapor particle separator, wherein the heater includes a radiant heater that surrounds the metallic tube to provide a heating chamber.

5. The vapor particle separator of claim 1, wherein the micro porous membrane is composed of a metal selected from the group consisting of stainless steel, aluminum, titanium, zirconium and a combination thereof.

6. The vapor particle separator of claim 1, wherein the micro porous membrane has a pore size ranging from 5 nm to 50,000 nm.

7. The vapor particle separator of claim 1, wherein the micro porous membrane comprises at least two layers, wherein a first layer of the at least two layers has a first thickness ranging from 5 microns to 20 microns and has a first pore size ranging from 5 nm to 500 nm and a second layer of the at least two layers has a second pore size ranging from 500 nm to 50,000 nm and a second thickness ranging from 20 microns to 400 microns.

8. The vapor particle separator of claim 1, wherein the micro porous membrane has a tube geometry, wherein one of the at least one particle passageway is centrally positioned in the separation chamber.

9. The vapor particle separator of claim 8, wherein the tube geometry has a substantially circular cross section across a length of the micro-porous membrane extending from the entrance to the separation chamber to the particle exit of the separation chamber, or the tube geometry has a multi-sided cross section across the length of the micro-porous membrane extending from the entrance to the separation chamber to the particle exit of the separation chamber.

10. The vapor particle separator of claim 9, wherein the at least one vapor passageway is an outer tube wherein an inner wall of the outer tube is provided by the micro porous membrane.

11. The vapor particle separator of claim 1 further comprising a first pump for applying a first vacuum to the vapor exit of the separation chamber.

12. The vapor particle separator of claim 11 further comprising a second pump for applying a second vacuum to the particle exit of the separation chamber.

13. The vapor particle separator of claim 12, wherein application of the first vacuum and the second vacuum provides a cross flow filtration.

14. The vapor particle separator of claim 1 further comprising a probe for collecting the particulates of the exhaust gas from an exhaust plumb of an engine and for introducing the particulates of the exhaust gas to the temperature controlled chamber of the vapor particle separator.

15. The vapor particle separator of claim 1 further comprising a filter for collecting the gas phase molecules from the vapor exit of the vapor particle separator, wherein the filter is selected from the group consisting of activated carbon filters, zeolites, polymers and a combination thereof.

16. A method of separating vapors from particles comprising:
- collecting particulates of an exhaust gas from an exhaust plume of an engine;
- heating the particles of the exhaust gas in a temperature controlled chamber of a vapor particle separator, wherein a temperature of the temperature controlled chamber is selected to desorb gas phase molecules from the particulates of the exhaust gas;
- introducing the particles of the exhaust gas and the gas phase molecules that were desorbed from the particles of the exhaust gas into a separation chamber of the vapor particle separator that includes a particle passageway to a particle exit in a first direction and an vapor passageway to a vapor exit in a second direction, wherein an interface between the particle passageway and the vapor passageway is provided by a micro porous membrane; and
- applying a cross flow to the separation chamber to draw the vapors from the vapor exit of the vapor particle separator and to draw the particles of the exhaust gas from the particle exit of the vapor particle separator.

17. The method of claim 16, wherein the particulates of the exhaust gas are selected from the group consisting of linear alkanes, polyaromatic hydrocarbons, elemental carbons, and a combination thereof.

18. The method of claim 17, wherein the particulates of the exhaust gas have a particle size ranging from 5 nm to 500 nm.

19. The method of claim 17, wherein the gas phase molecules desorbed from the particulates of the exhaust gas are selected from the group consisting of linear alkanes, elemental carbons, polyaromatic hydrocarbons, and a combination thereof.

20. The method of claim 16, wherein the temperature of the temperature controlled chamber to desorb the gas phase molecules from the particulates of the exhaust gas ranges from 20° C. to 500° C.

21. The method of claim 16, wherein the micro porous membrane has a pore size ranging from 5 nm to 50,000 nm.

22. The method of claim 16, wherein the micro porous membrane comprises at least two layers, wherein a first layer of the at least two layers has a first thickness ranging from 5 microns to 20 microns and has a first pore size ranging from 5 nm to 500 nm and a second layer of the at least two layers has a second pore size ranging from 500 nm to 50,000 nm and a second thickness ranging from 20 microns to 400 microns.

23. The method of claim 16, wherein the micro porous membrane has a tube geometry, wherein one of the at least one particle passageway is centrally positioned in the separation chamber.

24. The method of claim 16, wherein the first direction of particle passageway is a longitudinal direction through the vapor particle separator and the second direction of the vapor passageway is an axial direction that is substantially perpendicular to the longitudinal direction.

25. The method of claim 24, further comprising a first pump to apply a first flow to the vapor exit of the vapor particle passageway and a second pump to apply a second flow to the particle exit of the vapor particle passageway, wherein application of the first flow and the second flow through the vapor exit and particle exit provides cross flow filtration through the separation chamber of the vapor particle separator.

26. The method of claim 25, wherein the first pump provides a flow rate ranging from 0.1 lpm to 5 lpm, and the second pump provides a flow rate ranging from 0.1 lpm to 5 lpm.

27. The method of claim 16, further comprising applying filter to the vapor exit for collecting the gas phase molecules from the vapor exit of the vapor particle separator.

28. The method of claim 16, further comprising applying sweeping gas to the vapor particle separator that is selected from the group consisting of nitrogen, argon and a combination thereof.

* * * * *